US008748391B2

(12) United States Patent
Cumberlidge et al.

(10) Patent No.: US 8,748,391 B2
(45) Date of Patent: *Jun. 10, 2014

(54) β-TURN PEPTIDOMIMETIC CYCLIC COMPOUNDS FOR TREATING DRY EYE

(75) Inventors: Garth Cumberlidge, Gloucester, MA (US); Karen Meerovitch, Cote Saint-Luc (CA); Teresa Lama, Montreal (CA)

(73) Assignee: Mimetogen Pharmaceuticals Inc., Montreal, Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/601,258

(22) Filed: Aug. 31, 2012

(65) Prior Publication Data

US 2012/0322747 A1     Dec. 20, 2012

Related U.S. Application Data

(63) Continuation of application No. 12/935,217, filed as application No. PCT/US2009/002121 on Apr. 3, 2009, now Pat. No. 8,293,713.

(60) Provisional application No. 61/208,873, filed on Feb. 27, 2009, provisional application No. 61/123,036, filed on Apr. 4, 2008.

(51) Int. Cl.
| | | |
|---|---|---|
| *A61K 38/00* | (2006.01) | |
| *A61P 9/10* | (2006.01) | |
| *A61P 27/02* | (2006.01) | |
| *A61K 38/12* | (2006.01) | |
| *A61K 31/395* | (2006.01) | |

(52) U.S. Cl.
CPC ............... *A61K 31/395* (2013.01); *A61K 38/12* (2013.01)
USPC ........................................ 514/20.1; 514/21.1

(58) Field of Classification Search
CPC .............................. A61K 31/395; A61K 38/12
See application file for complete search history.

(56) References Cited

U.S. PATENT DOCUMENTS

| 5,545,617 A | 8/1996 | Dartt et al. | |
|---|---|---|---|
| 6,881,719 B2 | 4/2005 | Saragovi et al. | |
| 8,293,713 B2 * | 10/2012 | Cumberlidge et al. | 514/20.8 |
| 2009/0318335 A1 | 12/2009 | Vitagliano et al. | |

FOREIGN PATENT DOCUMENTS

| EP | 1734052 A1 | 12/2006 | | |
|---|---|---|---|---|
| JP | 2001-064198 A | 3/2001 | | |
| WO | WO 91/01715 | * | 2/1991 | ............... A61K 9/06 |
| WO | WO 99/32135 | * | 1/1999 | ............. A61K 38/16 |
| WO | 01/52843 A1 | 7/2001 | | |
| WO | 2008056217 A1 | 5/2008 | | |
| WO | 2008/070132 A2 | 6/2008 | | |
| WO | 2009/123761 A1 | 10/2009 | | |

OTHER PUBLICATIONS

Maliartchouk et al. A Designed Peptidomimetic Agonistic Ligand of TrkA Nerve Growth Factor Receptors. The American Society for Pharmacology and Experimental Therapeutics, 2000. vol. 57, No. 2, pp. 385-391.*
Feng et al. Solid-Phase SnAr Macrocyclizations to Give Turn-Extended-Turn Peptidomimetics. Chem. Eur. J. 1999, vol. 5, No. 11, pp. 3261-3272.*
Burgess. Solid-Phase Syntheses of beta-Turn Analogues to Mimic or Disrupt Protein-Protein Interactions. Acc. Chem. Res. 2001, vol. 34, pp. 826-835.*
BD Phosphate Buffered Saline (pH 7.2) BD Saline Solution (0.9%), Aug. 2003, 3 pages.*
Water for Pharmaceutical Purposes. Pharmacopeial Forum, 2004, vol. 30, No. 5, 41 pages.*
Kobayashi et al. An experimental study on the shear viscosity of solids, J Appl Phys, 1996, vol. 80, No. 1, pp. 122-130.*
SARcode Bioscience, Lifitegrast 5.0% Ophthalmic Solution for Dry Eye Disease, Charles P. Semba, MD, FACR, FACC, Chief Medical Officer, SARcode Bioscience, Nov. 8, 2012, pp. 1-16.*
Feng, Y., et al., Solid-Phase S(N subscript)Ar Macrocyclizations to Give Turn—Extended-Turn Peptidomimetics, Chem. Eur. J., 1999, 5(11):3261-3272.
Feng, Y., et al., S(N subscript)Ar Cyclizations to Form Cyclic Peptidomimetics of beta-Turns, J. Am. Chem. Soc., 1998, 120:10768-10769.
Feng, Y., et al., Steriochemical Implications on Diversity in beta-Turn Peptidomimetic Libraries, J. Org. Chem., 1999, 64:9175-9177.
Wang, Z., et al., Conformations of Peptidomimetics Formed by S(N subscript)Ar Macrocylizations: 13- to 16-Membered Ring Systems, Chem. Eur. J., 1999, 5(11):3273-3278.
Afonso, A.A., et al., Correlation of Tear Fluorescein Clearance and Schirmer Test Scores wth Ocular Irritation Symptoms, Ophthalmology, 1999, 106(4):803-810.
Apfel, S.C., Nerve Growth Factor for the Treatment of Diabetic Neuropathy: What Went Wrong, What Went Right, and What does the Future Hold?, Int. Rev. Neurobiol., 2002, 50:393-413.
Bonini, S, et al., Topical Treatment with Nerve Growth Factor for Neurotrophic Keratitis, Opthalmology, 2000, 107:1347-1352.
Chen, W., et al., Keratoconjunctivitis Sicca Modifies Epithelial Stem Cell Proliferation Kinetics in Conjunctiva, Cornea, 2007, 26(9):1101-1106.
Coassin, M., et al., Efficacy of Topical Nerve Growth Factor Treatment in Dogs Affected by Dry Eye, Graefe's Arch. Clin. Exp. Opthalmol., 2005, 243(2):151-155.
Dartt, D., et al., Regulation of Conjunctival Goblet Cell Secretion by Ca(superscript)2+ and Protein Kinase C, Exp. Eye. Res., 2000, 71:619-628.
Database WPI Week 200137, Thomson Scientific, London, GB; AN 2001-347758 No. XP002539482, Mar. 13, 2001. (Abstract).

(Continued)

*Primary Examiner* — Marcela M Cordero Garcia
(74) *Attorney, Agent, or Firm* — Pillsbury Winthrop Shaw Pittman LLP

(57) ABSTRACT

The present invention relates to methods of treating dry eye using β-turn peptidomimetic cyclic compounds or derivatives thereof. The β-turn peptidomimetic cyclic compounds can be used alone, in combination and/or in conjunction with one or more other compounds, molecules or drugs that treat dry eye.

21 Claims, 27 Drawing Sheets

(56) References Cited

OTHER PUBLICATIONS

Esquenazi, S., et al., Topical Combination of NGF and DHA Increases Rabbit Corneal Nerve Regeneration after Photorefractive Keratectomy, IOVS, 2005, 46(9):3121-3127.

Joseph, E.K., et al., MU and Delta Opioid Receptors on Nociceptors Attenuate Mechanical Hyperalgesia in Rat, Neuroscience, 2010, 171:344-350.

Lambiase, A., et al., Experimental and Clinical Evidence of Neuroprotection by Nerve Growth Factor Eye Drops: Implications for Glaucoma, PNAS, 2009, 106(32):13469-13474.

Lambiase, A., et al., Topical Treatment with Nerve Growth Factor for Corneal Neurotrophic Ulcers, New England Journal of Medicine, 1998, 338(17):1174-1180.

Lewin, G.R., et al., Nerve Growth Factor-Induced Hyperalgesia in the Neonatal and Adult Rat, The Journal of Neuroscience, 1993, 13(5):2136-2148.

Maliartchouk, S., et al., A Designed Peptidomimetic Agonistic Ligand of TrkA Nerve Growth Factor Receptors, Molecular Pharmacology, 2000, 57(2):385-391.

Micera, A.M., et al., Nerve Growth Factor and Tissue Repair Remodeling: trkA$^{NGFR}$ and p75$^{NTR}$, Two Receptors One Fate, Cytokine & Growth Factor Reviews, 2007, 18:245-256.

Petty, B.G., et al., The Effect of Systemically Administered Recombinant Human Nerve Growth Factor in Healthy Human Subjects, Annals of Neurology, 1994, 36(2):244-246.

Rios, J.D., et al., Immunolocalization of Muscarinic and VIP Receptor Subtypes and their Role in Stimulating Goblet Cell Secretion, IOVS, 1999, 40(6):1102-1111.

Rios, D.J., et al., Role of Neurotrophins and Neurotrophin Receptors in Rat Conjunctival Goblet Cell Secretion and Proliferation, IOVS, 2007, 48(4):1543-1551.

Rukwied, R., et al., NGF Induces Non-Inflammatory Localized and Lasting Mechanical and Thermal Hypersensitivity in Human Skin, Pain, 2010, 148:407-413.

Shatos, M, et al., Isolation, Characterization, and Propagation of Rat Conjunctival Goblet Cells in Vitro, IOVS, 2001, 42(7):1455-1464.

The Ocular Surface, The Definition and Classification of Dry Eye Disease: Report of the Definition and Classification Subcommittee of the International Dry Eye Workshop (2007), 5(2):75-92.

The Ocular Surface, The Epidemiology of Dry Eye Disease: Report of the Epidemiology Subcommittee of the International Dry Eye Workshop (2007), 5(2):93-107.

Viau, S., et al., Time Course of Ocular Surface and Lacrimal Gland Changes in a New Scopolamine-Induced Dry Eye Model, Graefes Arch. Clin. Exp. Ophthalmol., 2008, 246:857-867.

Zaccaro, et al., Selective Small Molecule Peptidomimetic Ligands of TrkC and TrkA Receptors Afford Discrete or Complete Neurotrophic Activities, Chemistry and Biology, 2005, 12(9):1015-1028.

Notification of Transmittal of the International Search Report and the Written Opinion of the International Searching Authority or the Declaration for International Application No. PCT/US2009/002121, dated Aug. 7, 2009.

Notification Concerning Transmittal of International Preliminary Report on Patentability for International Application No. PCT/US2009/002121, dated Oct. 14, 2010.

Colangelo, A.M., A New Nerve Growth Factor-Mimetic Peptide Active on Neuropathic Pain in Rats, 2008, J. of Neuroscience, 28(11):2698-2709.

Meerovitch, K., et al., Safety and Efficacy of MIM-D3 Ophthalmic Solutions in a Randomized, Placebo-Controlled Phase 2 Clinical Trial in Patients With Dry Eye, Clinical Ophthalmology, 2013(7):1275-1285 (2013).

Allergan, Inc., Highlights of Prescribing Information for "Restatsis", revised Jun. 2013, www.allergan.com/products/patent_notices.

Semba, C.P., et al., A Phase 2 Randomized, Double-Masked, Placebo-Controlled Study of a Novel Integrin Antagonist (SAR 1118) for the Treatment of Dry Eye, Am. J. Ophthalmol., 2012;xx:xxx. Article in press: doi:10.1016/j.ajo.2011.11.003.

* cited by examiner

D.

| Code | aa | Scaffold | X |
|------|-----|----------|---|
| 1Aa | IK | amine | amine |
| 1Ad | EK | amine | amine |
| 1Ba | IK | amine | guanidine |
| 3Aa | IK | ether | amine |
| 3Ac | GK | ether | amino |
| 3Ae | IR | ether | amine |
| 3Ak | RG | ether | amino |
| 3Ba | IK | ether | guanidine |
| 3Bg | KG | ether | guanidine |
| 3Bi | KT | ether | guanidine |
| 3Ca | IK | ether | methylsulfonamide |
| 3Ce | IR | ether | methylsulfonamide |
| 3Cg | KG | ether | methylsulfonamide |
| 3Ck | RG | ether | methylsulfonamide |

β-turn Peptidomimetic Cyclic

FIG. 1D

|  |  | Rat 1 | Rat 2 | Rat 3 | Rat 4 | Average | sem |
|---|---|---|---|---|---|---|---|
| NGF | 1 nM | 1.1 | 1.6 | 1.5 | 1.2 | 1.3 | 0.1 |
| Cch | 100 µM | 2.1 | 1.0 | 1.0 | 1.1 | 1.3 | 0.3 |
| MIM-D3 | 30 µM | 3.8 | 0.6 | 0.9 | 1.7 | 1.7 | 0.7 |
|  | 10 µM | 2.3 | 0.9 | 1.6 | 1.7 | 1.6 | 0.3 |
|  | 1 µM | 1.8 | 1.6 | 1.9 | 1.2 | 1.6 | 0.2 |
|  | 0.3 µM | 1.9 | 1.4 | 0.7 | 1.3 | 1.3 | 0.2 |
| MIM-3Aa | 30 µM | 3.3 | x0.05 | 1.0 | 1.9 | 2.1 | 0.7 |
|  | 10 µM | 2.9 | 1.5 | 1.1 | 1.2 | 1.7 | 0.4 |
|  | 1 µM | 2.0 | 0.9 | 2.2 | 1.5 | 1.6 | 0.3 |
|  | 0.3 µM | 3.0 | 2.0 | 1.8 | 1.4 | 2.1 | 0.3 |
| MIM-3Ak | 30 µM | 1.3 | 0.3 | 1.0 | 1.8 | 1.1 | 0.3 |
|  | 10 µM | 1.0 | 1.5 | 1.1 | 1.3 | 1.2 | 0.1 |
|  | 1 µM | 0.8 | 0.3 | 1.9 | 1.5 | 1.1 | 0.3 |
|  | 0.3 µM | 1.0 | 2.3 | 1.3 | 1.1 | 1.4 | 0.3 |

FIG. 2

Growth and Morphology of Goblet Cells in Culture

A

B

C

Histochemical Analysis of Primary Cultures of Goblet Cells to PAS

Effect of PMA, NGF and MIM-D3 on MAPK Activity

Quantitation of MAPK Activation Relative to Total Actin Protein

Bar Graph Showing the Mucin Concentration Prior to and After Topical MIM-D3 and NGF Treatment in Normal Rats Bar Graph Showing the Change in Mucin Concentration from Baseline
After Topical MIM-D3 and NGF Treatment in Normal Rats

Study Design and Scheduled of Endpoint Evaluations

| | Day | Scopolamine | Dosing | Body Weight | Schirmer | Fluorescein Clearance | TBUT | Corneal Staining | Mucin |
|---|---|---|---|---|---|---|---|---|---|
| | -1 | | | X | X | X | | | |
| | 0 | X | | | | | | | |
| Week 1 | 1 | X | | | | | | | |
| | 2 | X | | | X | X | | | |
| | 3 | X | | | | | | | |
| | 4 | X | | | | | | | |
| | 5 | X | X | | X | X | | | |
| | 6 | X | X | | | | | | |
| | 7 | X | X | X | X | X | | | |
| Week 2 | 8 | X | X | | | | | | |
| | 9 | X | X | | | | | | |
| | 10 | X | X | | | | | | |
| | 11 | X | X | | | | | | |
| | 12 | X | X | | | | | | |
| | 13 | X | X | | | | X | X | X |
| | 14 | X | X | X | X | X | | | |
| Week 3 | 15 | X | X | | | | | | |
| | 16 | X | X | | | | | | |
| | 17 | X | X | | | | | | |
| | 18 | X | X | | | | | | |
| | 19 | X | X | | | | | | |
| | 20 | X | X | | | | X | X | X |
| | 21 | X | X | X | X | X | | | |
| Week 4 | 22 | X | | | | | | | |
| | 23 | X | | | | | | | |
| | 24 | X | | | | | | | |
| | 25 | X | | | | | | | |
| | 26 | X | | | | | | | |
| | 27 | X | | | | | X | X | X |
| | 28 | X | | X | X | | | | |
| | 29 | X | | | | | | | |

FIG. 16

β-TURN PEPTIDOMIMETIC CYCLIC COMPOUNDS FOR TREATING DRY EYE

RELATED APPLICATIONS

This application is a continuation application of U.S. application Ser. No. 12/935,217, filed Sep. 28, 2010, which is a 371 of International Application No. PCT/US2009/002121, filed Apr. 3, 2009, which claims the benefit of priority to U.S. Provisional Application Nos. 61/208,873, filed Feb. 27, 2009, and 61/123,036 filed Apr. 4, 2008, all of which applications are expressly incorporated herein by reference in their entirety.

BACKGROUND OF THE INVENTION

Dry eye, also know as keratoconjunctivitis sicca, is a multifactorial disease of the tears and ocular surface that results in symptoms of discomfort, visual disturbance, and tear film instability with potential damage to the ocular surface. It is accompanied by increased osmolarity of the tear film and inflammation of the ocular surface (*The Ocular Surface*, "The Definition and Classification of Dry Eye Disease: Report of the Definition and Classification Subcommittee of the International Dry Eye Workshop (2007)," 5(2): 75-92 (2007)). Dry eye is recognized as a disturbance of the lacrimal functional unit, an integrated system comprising the lacrimal glands, ocular surface (cornea, conjunctiva and meibomian glands) and lids, and the sensory and motor nerves that connect them. The lacrimal functional unit controls the major components of the tear film in a regulated fashion and responds to environmental, endocrinological, and cortical influences. The unit's function is to preserve the integrity of the tear film, the transparency of the cornea, and the quality of the image projected onto the retina. Disease or damage to any component of the lacrimal functional unit (the afferent sensory nerves, the efferent autonomic and motor nerves and the tear-secreting glands) can destabilize the tear film and lead to ocular surface disease that expresses itself as dry eye.

The major classes of dry eye are aqueous tear-deficient dry eye (ADDE) and evaporative dry eye (EDE). ADDE is due to failure of lacrimal tear secretion and this class can be further subdivided to Sjogren syndrome dry eye (the lacrimal and salivary glands are targeted by an autoimmune process, e.g., rheumatoid arthritis) and non-Sjögren's syndrome dry eye (lacrimal dysfunction, but the systemic autoimmune features of Sjögren's syndrome are excluded, e.g., age-related dry eye). EDE is due to excessive water loss from the exposed ocular surface in the presence of normal lacrimal secretory function. Its causes can be intrinsic (due to intrinsic disease affecting lid structures or dynamics, e.g., meibomian gland dysfunction) or extrinsic (where ocular surface disease occurs due to some extrinsic exposure, e.g., vitamin A deficiency) (See *The Ocular Surface*, "The Definition and Classification of Dry Eye Disease: Report of the Definition and Classification Subcommittee of the International Dry Eye Workshop (2007)," 5(2): 75-92 (2007)).

Dry Eye is one of the most common ocular problems with an estimated prevalence of 4.91 million people in the United States affecting around 3.23 million women and 1.68 million men over the age of fifty (*The Ocular Surface*, "The Epidemiology of Dry Eye Disease," 5(2): 93-107 (2007)). Current therapies for dry eye are palliative with a focus on the replacement of tears to reduce symptoms. Over-the-counter artificial tear formulations are available. In addition, a non-pharmacological approach for improving aqueous tear film content is punctual tamponade occlusion. However, punctual tamponade occlusion carries the risk of reduced tear production, clearance and ocular surface sensation. While these palliative therapies have benefits over the short term, they have limited utility in long-term control therapy for dry eye. RESTASIS® (cyclosporine A) is the first prescription product for dry eye therapy. RESTASIS® increases tear production in patients whose tear production is suppressed as a result of ocular inflammation associated with dry eye disease. However, there is a need for therapies that have a broader application than anti-inflammatory medication.

Several clinical studies have found that topical NGF improves the corneal sensitivity in dry eye and increases the number of conjunctival goblet cell density in a study of dogs with surgically induced dry eye (Bonini, S., et al., "Topical Treatment with Nerve Growth Factor for Neurotrophic Keratitis," Ophthalmology, 107: 1347-1352 (2000)). However, due to the fact that NGF stimulates neurite sprouting by neural cells, one of the side effects of administration of topical NGF is ocular pain (Bonini, S., et al., "Topical Treatment with Nerve Growth Factor for Neurotrophic Keratitis," Ophthalmology, 107: 1347-1352 (2000)). In addition, NGF has poor pharmacokinetics and bioavailability and the costs for manufacturing are high. A need exists in the art for alternative methods of treating dry eye.

SUMMARY OF THE INVENTION

The invention provides a method of treating dry eye in a subject in need thereof comprising administering to said subject an effective amount of a β-turn peptidomimetic cyclic compound. In one embodiment, the β-turn peptidomimetic cyclic compound comprises a macrocyclic ring of 13 to 17 carbon atoms. In a more particular embodiment, the β-turn peptidomimetic cyclic compound is represented by structural Formula (I):

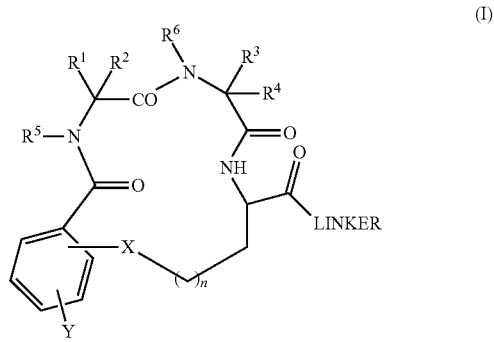

wherein $R^1$ and $R^3$ are independently selected from hydrogen, $C_1$ to $C_6$ alkyl, aryl or an amino acid side chain substituent found in the twenty protein-amino acids, in either enantiomeric configuration; $R^2$ and $R^4$ are independently hydrogen or $C_1$ to $C_6$ alkyl; or $R^1$ and $R^2$ together with the carbon atom to which they are attached form a cyclopropyl, cyclobutyl, cyclopentyl or cyclohexyl group; or $R^3$ and $R^4$ together with the carbon atom to which they are attached form a cyclopropyl, cyclobutyl, cyclopentyl or cyclohexyl group; $R^5$ and $R^6$ are hydrogen or $C_1$ to $C_6$ alkyl; Y is hydrogen or one or two aromatic substituents; X is selected from O, N, S, P, Se, C, alkylene of 1 to 6 carbon atoms, SO, $SO_2$ or NH; n is 0, 1, 2, 3, 4 or 5; and LINKER is a linking group effective to form dimers of the compound of formula (I) by reaction with a homo bifunctional compound. Suitable LINKER groups include, but are not limited to, NH$_2$, OH, SH, COOH, CH$_3$CO, CHO, and NH—CH$_2$—COOH.

In another embodiment of the present invention X is O, S or NH, R$^1$, R$^3$, R$^5$ and R$^6$ are each hydrogen atoms and the macrocyclic ring has 14, 15 or 16 ring atoms.

In another embodiment, R$^1$ and R$^3$ are derived from a sequence of different proteinogenic amino acids side chains.

In another embodiment of the present invention, X is O, S or NH.

In a particular embodiment, the β-turn peptidomimetic cyclic compound of Formula I is represented by the following Formula:

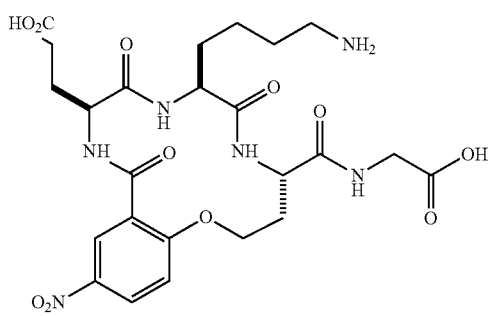 [SMILES: NCCCC[C@@H]1NC(=O)[C@H](CCC(=O)O)NC(=O)c2cc([N+](=O)[O-])ccc2OCC[C@@H](C(=O)NCC(=O)O)NC1=O]

or a pharmaceutically acceptable salt thereof. The compound is referred to herein as D3. D3 has been demonstrated to possess Trk modulator activity.

In another embodiment, the β-turn cyclic compound is selected from the group consisting of:

1Ad

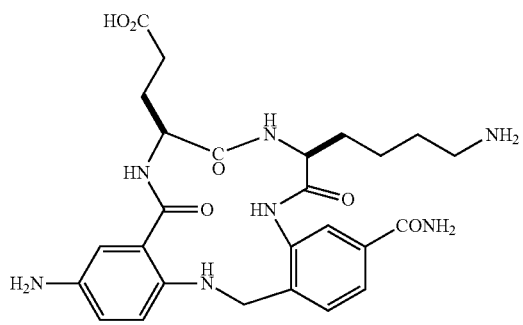

3Aa

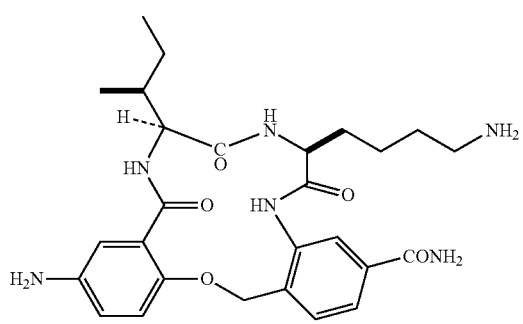

3Ak

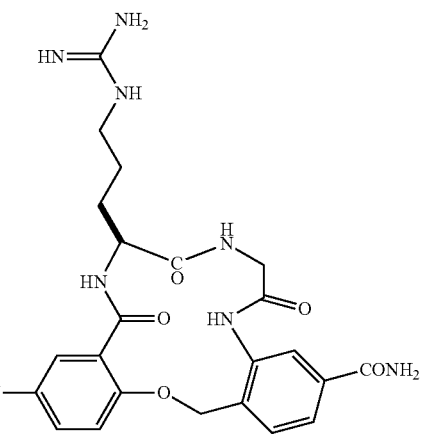

3Ba

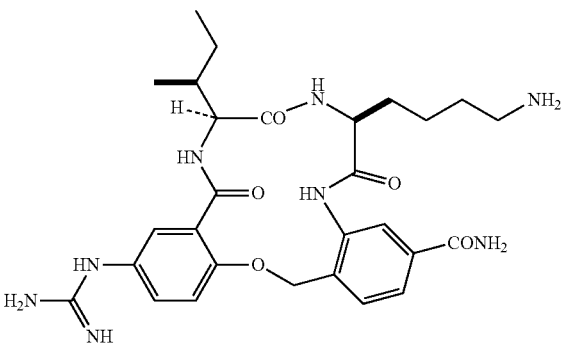

3Bg

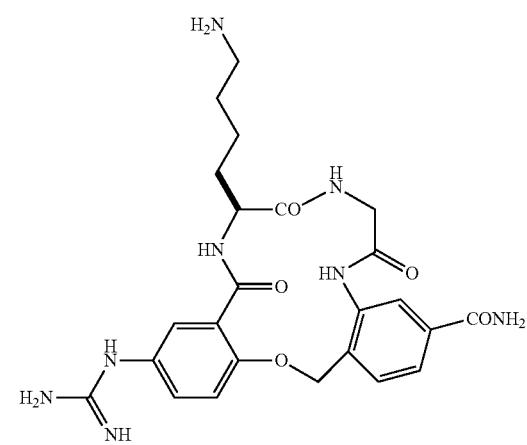

3Bi
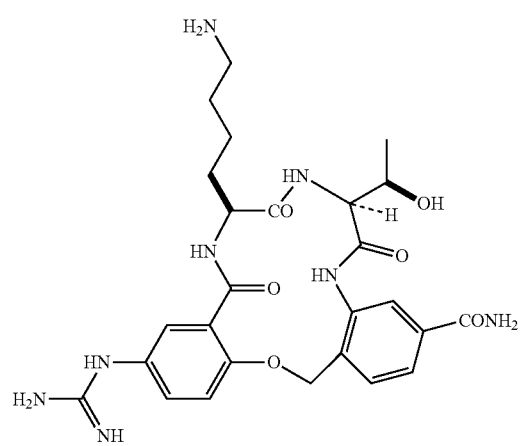
3Ca
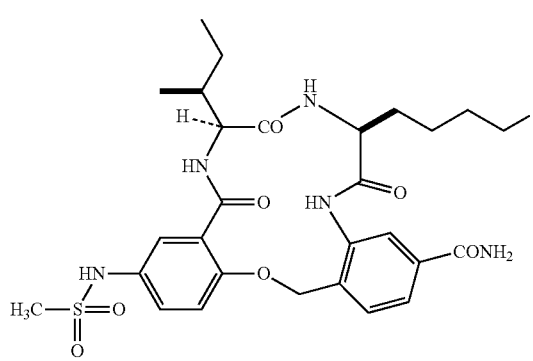
3Ce
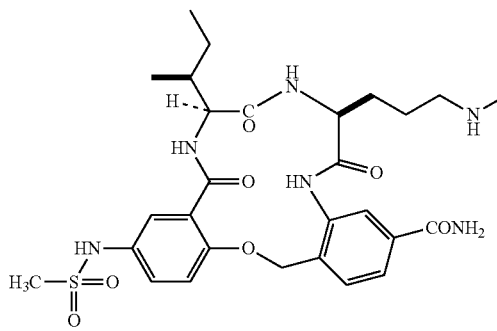
3Cg
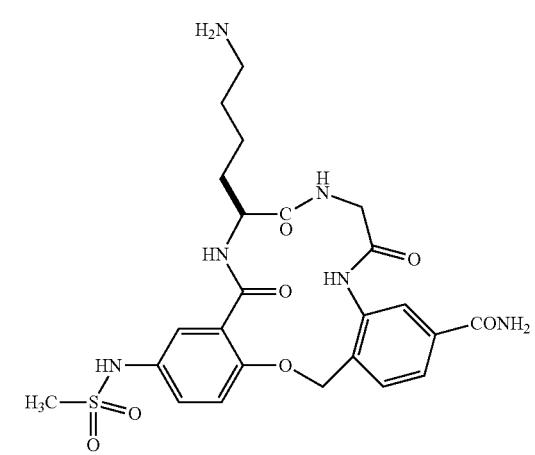
3Ck
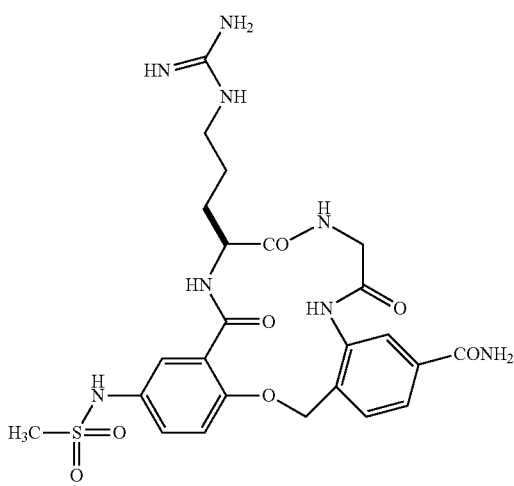
1Aa
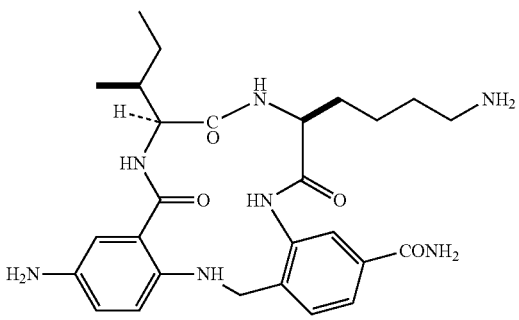
1Ba
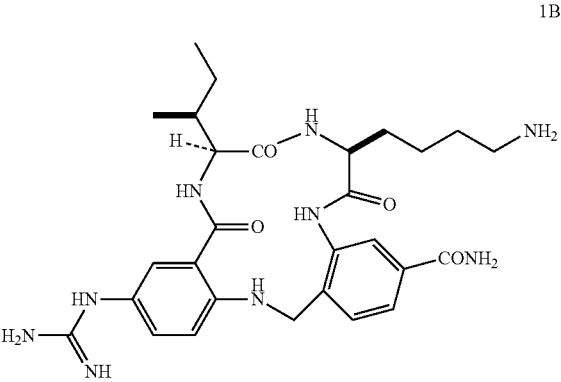
3Ac
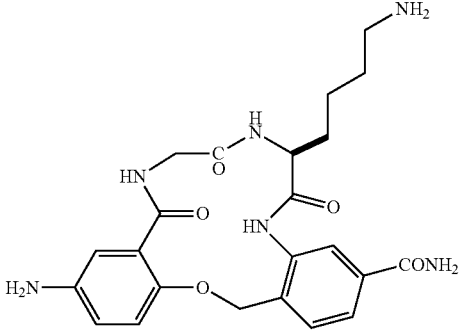
and

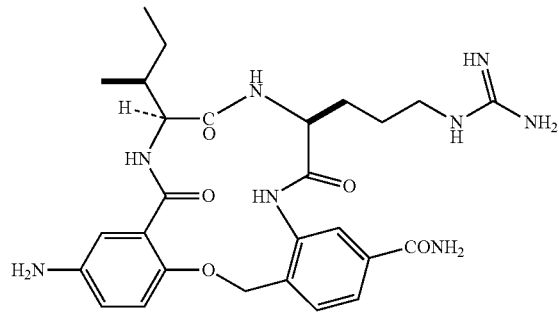

3Ae or a pharmaceutically acceptable salt of any of the foregoing. These compounds can possess Trk modulator activity.

In one embodiment, the invention relates to a method of treating dry eye in a subject in need thereof comprising administering to said subject an effective amount of a β-turn peptidomimetic cyclic compound represented by the following structural Formula (D3):

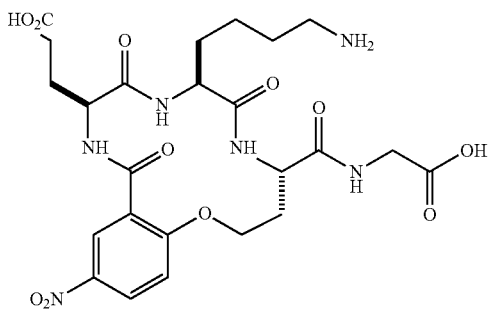 [SMILES: NCCCC[C@@H]1NC(=O)[C@H](CCC(=O)O)NC(=O)c2cc([N+](=O)[O-])ccc2OCC[C@@H](C(=O)NCC(=O)O)NC1=O]

or a pharmaceutically acceptable salt thereof.

In another embodiment, the invention relates to a method of treating dry eye in a subject in need thereof comprising administering to said subject an effective amount of a β-turn peptidomimetic cyclic compound represented by Formula 3Aa:

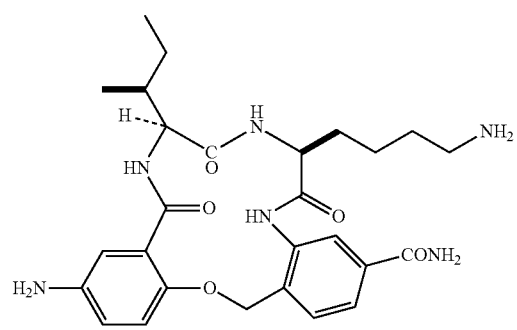

3Aa or a pharmaceutically acceptable salt thereof.

In yet another embodiment, the invention relates to a method of treating dry eye in a subject in need thereof comprising administering to said subject an effective amount of a β-turn peptidomimetic cyclic compound represented by Formula 3Ak:

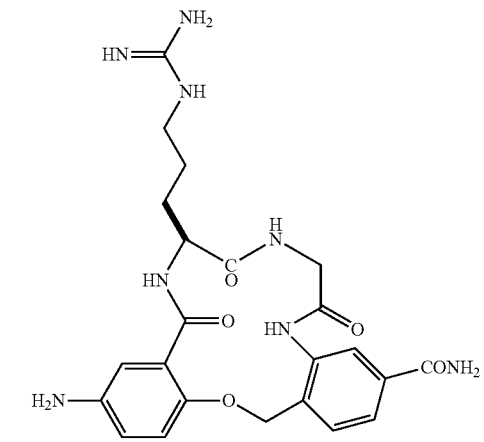

3Ak or a pharmaceutically acceptable salt thereof.

In one embodiment, the invention relates to a method of stimulating mucin secretion in a subject in need thereof comprising administering to said subject an effective amount of a β-turn peptidomimetic cyclic compound described herein.

The invention further relates to the use of a compound described herein (e.g. a β-turn peptidomimetic cyclic compound) for the manufacture of a medicament for treating dry eye in a subject in need of treatment.

The invention further relates to a pharmaceutical composition useful for treating dry eye in a subject in need of treatment. The pharmaceutical composition comprises a compound described herein (e.g., β-turn peptidomimetic cyclic compound) and a pharmaceutically acceptable carrier.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

In the description of the Figures and the supporting experiments, the compound identifications include the prefix MIM. The compound identifications with the prefix are the same as the compound identifications absent the prefix. For example, COMPOUND D3, D3 and MIM-D3 refer to the same compound.

FIG. 1D illustrates the complete letter codes for β-turn peptidomimetic cyclic compounds including the backbone (1, 2 or 3), X-substituents (A, B, C or D) and dipeptide amino acids ($R^1$ and $R^2$).

FIG. 2 is a table of data from four experiments in conjunctival goblet cells of rats (Rats 1-4) testing nerve growth factor (NGF), carbachol (CCh), compound D3, compound 3Aa and compound 3Ak at doses of 30 μM (micromolar), 10 μM, 1 μM and 0.3 μM. The table shows the average (Avg) and standard error of measurement (SEM).

FIG. 5A shows that adherent cells are visible by day nine. FIG. 5B shows that single cells adhering to the tissue culture well exhibit cobblestone morphology and contain tiny translucent droplets in cytoplasmic vesicles. FIG. 5C open arrows show that as cells proliferated in culture, tiny droplets were observed to form on the surface of the goblet cells, suggestive of a mucus-like secretory product. FIG. 5C closed arrow shows that as these droplet-containing cells grew in culture, the droplets merged into pools.

FIG. 6A shows that the cells have positive reactivity to PAS. FIG. 6B open arrow shows that many cytoplasmic perinuclear vesicles were observed. FIGS. 6B and 6C closed arrows show that several of these vesicles stained intensely with PAS indicating the presence of neutral glycoconjugates within secretory granules.

FIG. 16 is a graph of the study design and schedule of endpoint evaluations from Example 3.

FIG. 20A shows the change in TBUT (sec) for the untreated group, saline group and the group treated with 1% compound D3 at Day 28 versus Day 13. FIG. 20B shows the change in corneal staining (Score) for the untreated group, saline group and the group treated with 1% compound D3 at Day 28 versus Day 13. FIG. 20C shows the change in mucin production (ng/μL) for the untreated group, saline group and the group treated with 1% compound D3 at Day 28 versus Day 13.

FIG. 21A shows the change in TBUT (sec±sem) (Y axis) for the saline group and the group treated with 1% compound D3 in days post scopolamine implantation (X axis). FIG. 21B shows the change in corneal staining (Score±sem) (Y axis) for the saline group and the group treated with 1% compound D3 in days post scopolamine implantation (X axis). FIG. 21C shows the change in mucin production (ng/μL±sem) (Y axis) for the saline group and the group treated with 1% compound D3 in days post scopolamine implantation (X axis).

DETAILED DESCRIPTION OF THE INVENTION

Figure 1A:
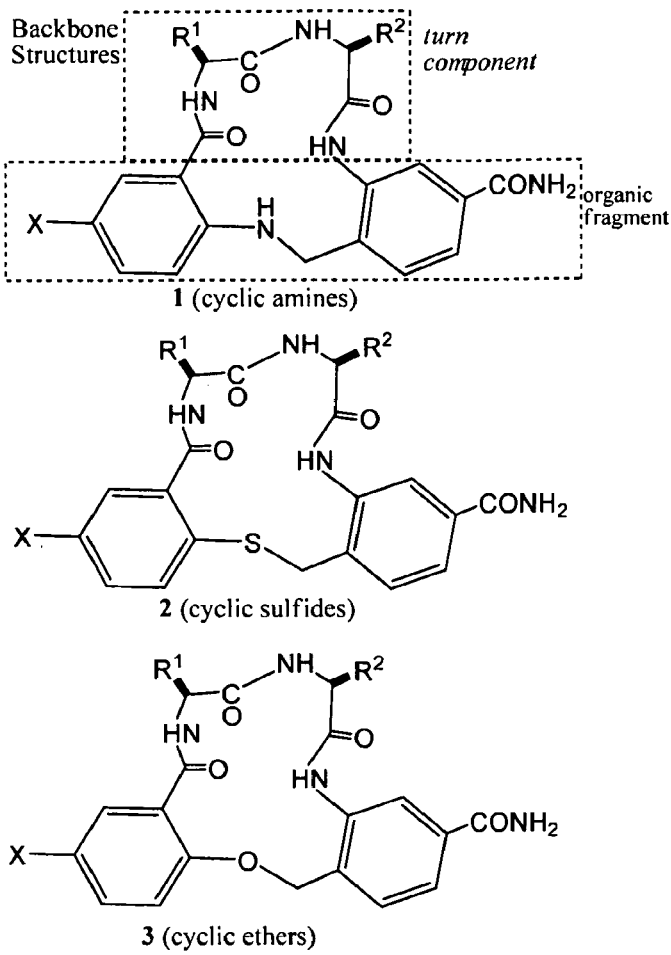
FIG. 1A is the code for the β-turn backbones, numbered 1, 2 and 3, for Trk modulator compounds.

The present invention relates to methods of treating dry eye in a subject in need thereof comprising administering to said subject a β-turn peptidomimetic cyclic compound. As used herein, a "β-turn peptidomimetic cyclic compound" refers to cyclic compounds, which mimic the β-turn region of neurotrophin receptor ligands (e.g., NGF, NT-3, NT-4 and BDNF). In a particular embodiment, the β-turn peptidomimetic cyclic compound of the present invention can be a neurotrophin tyrosine kinase (Trk) receptor modulator. In another particular embodiment, the β-turn peptidomimetic cyclic compound can be a p75 receptor modulator. In yet another embodiment, the β-turn peptidomimetic cyclic compound can be both a p75 receptor modulator and a Trk receptor modulator.

In one embodiment, the β-turn peptidomimetic cyclic compound is represented by structural Formula I. In a particular embodiment, the β-turn peptidomimetic cyclic compound is compound D3 or derivatives of compound D3.

In another embodiment, the β-turn peptidomimetic cyclic compound can be a compound selected from the group consisting of: 1Ad, 3Aa, 3Ak, 3Ba, 3Bg, 3Bi, 3Ca, 3Ce, 3Cg, 3Ck, 1Aa, 1Ba, 3Ac and 3Ae.

Although the β-turn peptidomimetic cyclic compound of the present invention can be a Trk receptor modulator compound or a p75 receptor modulator, the usefulness of the β-turn peptidomimetic cyclic compound in treating dry eye can rely on other activities such as modulating the TrkB receptor or any other receptor whose modulation is useful in treating dry eye. In addition, the usefulness of the β-turn peptidomimetic cyclic compound of the present invention in treating dry eye may rely on other modulations of neurotrophin-like activities such as, e.g., effects on the chemotactic recruitment of leukocytes, effects on granulocyte differentiation, effects on neutrophils, mast cells and eosinophils, effects on corneal epithelial cell proliferation, and upregulating selective sensory neuropeptides, substance P and calcitonin gene-related peptide.

As used herein a "Trk receptor modulator compound" is a TrkA receptor agonist, TrkC receptor agonist, or a compound that is both a TrkA receptor agonist and a TrkC receptor agonist.

As used herein "modulating" or "modulator" refers to agonizing or antagonizing a receptor.

As used herein a "p75 receptor modulator" is a p75 receptor agonist or antagonist.

Neurotrophins and Neurotrophin Receptors

Neurotrophins (NTFs) are a family of dimeric proteins that regulate the proliferation, survival, and differentiation of neurons in all vertebrate species. The NTFs include Nerve Growth Factor (NGF), Brain Derived Neurotrophic Factor (BDNF), Neurotrophin-3 (NT-3) and Neurotrophin-4 (NT-4). These NTFs bind to two transmembrane receptors, the high affinity receptor family tyrosine kinase (Trk) (TrkA, Trk B and Trk C) ($K_d$=10-100 μM) and the p75 receptor ($K_d$=1 nM). The Trk family receptor ligands are quite selective (e.g., NGF binds TrkA, BDNF binds TrkB; and NT-3 binds mainly TrkC).

Neurotrophins and their receptors have been identified in conjunctival goblet cells (CGCs) (Rios, J. D., et al., "Role of Neurotrophins and Neurotrophin Receptors in Rat Conjunctival Goblet Cell Secretion and Proliferation, *Ophthalmology & Visual Science*, 48: 1543-1551 (2007)). CGCs are the primary source of large soluble mucins in the tear film. These mucins provide a physical and chemical barrier that protects the cornea and conjunctiva from exogenous agents (bacterial or chemical) and facilitates the occurrence of a smooth refractive surface necessary for clear vision.

β-Turn Peptidomimetic Cyclic Compounds

In one embodiment, the β-turn peptidomimetic cyclic compound comprises a macrocyclic ring of 13 to 17 carbon atoms. In a more particular embodiment, the β-turn peptidomimetic cyclic compound is represented by structural Formula (I):

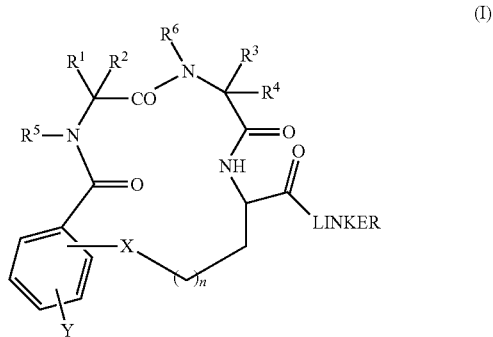

(I)

wherein $R^1$ and $R^3$ are independently selected from hydrogen, $C_1$ to $C_6$ alkyl, aryl or an amino acid side chain substituents found in the twenty protein-amino acids, in either enantiomeric configuration; $R^2$ and $R^4$ are independently hydrogen or $C_1$ to $C_6$ alkyl; or $R^1$ and $R^2$ together with the carbon atom to which they are attached form a cyclopropyl, cyclobutyl, cyclopentyl or cyclohexyl group; or $R^3$ and $R^4$ together with the carbon atom to which they are attached form a cyclopropyl, cyclobutyl, cyclopentyl or cyclohexyl group; $R^5$ and $R^6$ are hydrogen or $C_1$ to $C_6$ alkyl; Y is hydrogen or one or two aromatic substituents; X is selected from O, N, S, P, Se, C, alkylene of 1 to 6 carbon atoms, SO, $SO_2$ or NH; n is 0, 1, 2, 3, 4 or 5; and LINKER is a linking group effective to form dimers of the compound of formula (I) by reaction with a homo bifunctional compound. Suitable LINKER groups include, but are not limited to, $NH_2$, OH, SH, COOH, $CH_3CO$, CHO, and NH—$CH_2$—COOH.

The twenty amino-acid side chain substituents include the side chains of alanine, cysteine, aspartic acid, glutamic acid, phenylanine, glycine, histidine, isoleucine, lysine, leucine, methionine, asparagine, proline, glutamine, arginine, serine, threonine, valine, tryptophan, and tyrosine. For example, the side chain of glutamic acid is

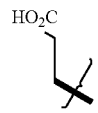

In another embodiment of the present invention X is O, S or NH, $R^1$, $R^3$, $R^5$ and $R^6$ are each hydrogen atoms and the macrocyclic ring has 14, 15 or 16 ring atoms.

In another embodiment, $R^1$ and $R^3$ are derived from a sequence of different protein amino acids side chains.

In another embodiment of the present invention, X is O, S or NH.

In a particular embodiment, the β-turn peptidomimetic cyclic compound is D3 (see Maliartchouk et al., *Mol Pharmcol* 57(2):385-391, 2000, which is incorporated herein by reference in its entirely and U.S. Pat. No. 6,881,719, which is incorporated herein by reference in its entirely), or derivatives of D3. A number of derivatives of D3 and other compounds of Formula I are envisioned for use in the methods of the invention and include simple modifications like biotinylated forms and molecules wherein two such units are linked by dimers. Other derivatives of D3 and other compounds of Formula I include side chains $R^1$-$R^6$ having amino acid side chain substituents found in the twenty protein-amino acids.

The side chains typical of the protein amino acids (e.g., Arg, Trp, His) allow for the formation/design of a diversity of structures that are easily generated derivatives of D3 and other compounds of Formula I, and they can include many types of functional groups.

The substituent(s) Y may be hydrogen or one or two aromatic substituents for example nitro, amino, halo, alkyl for example alkyl of 1 to 6, preferably 1 to 4 carbon atoms, and aryl for example phenyl or naphthyl. The alkyl and aryl substituents Y may be unsubstituted or substituted, suitable substituents being nitro and alkyl of 1 to 6 carbon atoms. Y may also be derivatized with a functional group, for example biotin. The group X may be any nucleophilic atom like O, N, S, P, Se, but also others such as C, or may be an alkylene radical typically of 1 to 6 carbon atoms, for example methylene; SO, $SO_2$ or NH. The point of connection could be ortho- or meta- to the benzoyl carbonyl. Permissible values of "n" are 0, 1, 2, 3, 4, and 5. The linking side chain that incorporates X is aliphatic as indicated in structure (I).

The side chain alkyl groups $R^1$, $R^2$, $R^3$, $R^4$, $R^5$, and $R^6$ can be varied in many ways to enhance the biological activities of these compounds. Typically $R^1$, $R^2$, $R^3$, and $R^4$ are amino acid side-chain substituents found in the twenty protein-amino acids, for example the side-chains of glutamic acid, lysine, ornithine and threonine, in either enantiomeric configuration. If the $R^1$ substituent is an amino acid side chain, the other substituent on that carbon, $R^2$, will typically be hydrogen, but could also be methyl, ethyl or benzyl. Alternatively, $R^1$ and $R^2$ together with their intervening atoms can be joined to give cyclopropane, cyclobutane, cyclopentane, and cyclohexane, residues. $R^3$ and $R^4$ are related in the same way as $R^1$ and $R^2$ as described above. That is, one of them will be an amino acid side chain with the other of these two substituents being hydrogen in most cases, but could also be methyl, ethyl, propyl or benzyl. In addition, $R^3$ and $R^4$ together with the intervening atoms can be joined to give cyclopropane, cyclobutane, cyclopentane, and cyclohexane, residues.

There is much scope for variation in $R^5$ and $R^6$ with the most common substituent at these positions being hydrogen or methyl. Those substituents can also be designed to correspond to one of the side chains of the twenty protein-amino acids, in particular, methyl.

Side chains found to be particularly conducive to biological activities are $R^1$ and $R^3$ as side chains of lysine, glutamic acid, tyrosine, iso-leucine, asparagine, and threonine, $R^2$, $R^4$, $R^5$, and $R^6$ as hydrogen. One or more of the side chains are selected especially to correspond to side chains within the turn regions of NGF.

In general, the macrocyclic compounds have 13 to 16 membered rings where the X substituent is O, N, S, SO, or $SO_2$.

In another embodiment, the β-turn peptidomimetic cyclic compound is selected from the group consisting of: 1Ad, 3Aa, 3Ak, 3Ba, 3Bg, 3Bi, 3Ca, 3Ce, 3Cg, 3Ck, 1Aa, 1Ba, 3Ac and 3Ae.

Figure 1B:
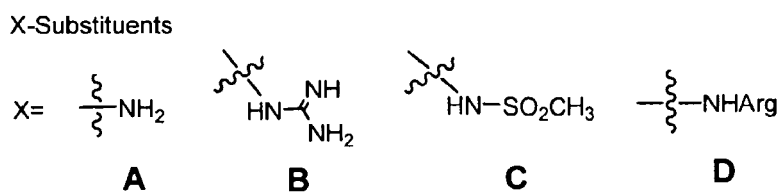
FIG. 1B is the code for X-substituents of the backbone, lettered A, B, C and D, for Trk modulator compounds.
Figure 1C:
FIG. 1C is the code for dipeptide $R^1$ and $R^2$ substituents of the backbone for Trk modulator compounds.

In yet another embodiment, the β-turn peptidomimetic cyclic compound is a compound comprising a cyclic amino, ether or sulfide scaffold (see FIG. 1A), with various substituents (e.g., amine, guanidine or methylsulfonamide) (see FIG. 1B) and $R^1$ and $R^2$ groups comprising dipeptide amino acid fragments (see FIG. 1C). (See also FIG. 1D).

In one embodiment, the invention relates to a method of stimulating mucin secretion in a subject in need thereof comprising administering to said subject an effective amount of a β-turn peptidomimetic cyclic compound described herein.

The compound of the present invention is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

As used herein, "dry eye" is a wide concept which is intended to include aqueous tear-deficient dry eye, evaporative dry eye, menopausal-associated dry eye, hypolacrimation, tear deficiency, xerophthalmia, Sjogren's syndrome, keratoconjunctivitis sicca, Stevens-Johnson syndrome, ocular pemphigoid, blepharitis marginal, lid-closure failure and sensory nerve paralysis, allergic conjunctivitis-associated dry eye, post-viral conjunctivitis dry eye, post-cataract surgery dry eye, chronic dry eye after laser in situ keratomileusis (LASIK), VDT operation-associated dry eye and contact lens wearing-associated dry eye, age-related dry eye, corneal injury, infection, Riley-Day syndrome, congenital alacrima, nutritional disorders or deficiencies (including vitamin), pharmacologic side effects, eye stress and glandular and tissue destruction, environmental exposure to smog, smoke, excessively dry air, airborne particulates, autoimmune and other immunodeficient disorders, and comatose patients rendered unable to blink. In addition, "dry eye" includes diseases caused by dry eye such as keratoconjunctival epithelial lesion, corneal epithelial sores, corneal ulcers (such as ulcers of corneal stromal layer) and ocular infectious disease.

Subject, as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species. In one embodiment, the subject is a human.

The term "treating" includes both therapeutic treatment and prophylactic treatment (reducing the likelihood of development). The term means decrease, suppress, attenuate, diminish, arrest, or stabilize the development or progression of a disease (e.g., a disease or disorder delineated herein), lessen the severity of the disease or improve the symptoms associated with the disease.

As used herein, the term pharmaceutically acceptable salt refers to a salt of the administered compounds prepared from pharmaceutically acceptable non-toxic acids including inorganic acids and organic acids thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

The invention further relates to pharmaceutical compositions for use in treating dry eye in a subject in need of treatment. The pharmaceutical composition comprises one or more β-turn peptidomimetic cyclic compounds of the present invention and a pharmaceutically acceptable carrier. Pharmaceutically acceptable carriers can also contain inert ingredients which do not interact with the regulatory/active substances in the compositions. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate, dextrose, ethanol, surfactants such as glycerol, or excipients.

In a further embodiment, the pharmaceutical composition further comprises an (i.e., one or more) additional therapeutic agent. An additional therapeutic agent suitable for use in the methods and pharmaceutical compositions described herein, can be, but is not limited to, for example: anti-inflammatory agents (e.g., RESTASIS® (Allergan)), mucin stimulants (e.g., Diquafasol (Inspire Pharmaceuticals) 15-(S)-HETE (Alcon), rebamipide (Otsuka) and ecabet (ISTA)), hormonal agents and lacrimal gland stimulants (e.g., androgen tears (Allergan)) and artificial tears.

MODES OF ADMINISTRATION

The composition can be formulated for topical ophthalmic application, for example, in the form of solutions, ointments, creams, lotions, eye ointments and, most preferably, eye drops or eye gels and can contain the appropriate conventional additives, including, for example, preservatives, solvents to assist drug penetration, and emollients in ointments and creams. Such topical formulations can contain compatible conventional carriers, for example cream or ointment bases, and ethanol or oleyl alcohol for lotions.

Alternatively, the active compounds may be applied to the eye via liposomes. Further, the active compounds may be infused into the tear film via a pump-catheter system. Another embodiment of the present invention involves the active compound contained within a continuous or selective-release device, for example, membranes such as, but not limited to, those employed in the pilocarpine (OCUSERT™) System (Alza Corp., Palo Alto, Calif.). As an additional embodiment, the active compounds can be contained within, carried by, or attached to contact lenses which are placed on the eye. Another embodiment of the present invention involves the active compound contained within a swab or sponge which can be applied to the ocular surface. Another embodiment of the present invention involves the active compound contained within a liquid spray which can be applied to the ocular surface. Another embodiment of the present invention involves an injection of the active compound directly into the lacrimal tissues or onto the eye surface.

When the pharmaceutical composition of the present invention for treating dry eye is used as an ophthalmic solution, it is provided in any dosage form which is used for ophthalmic solution, for example, an aqueous eye drop such as aqueous ophthalmic solution, aqueous suspended ophthalmic solution, viscous ophthalmic solution and solubilized ophthalmic solution, or a non-aqueous ophthalmic solution such as non-aqueous ophthalmic solution and non-aqueous suspended ophthalmic solution. Among these, the aqueous ophthalmic solution is preferable.

When the pharmaceutical composition of the present invention for treating dry eye is prepared into an aqueous ophthalmic solution, various additives normally used in the aqueous ophthalmic solution are conveniently contained therein as long as the object of the present invention is not adversely affected. Examples of such the additives include buffers, isotonizing agents, preservatives, solubilizers (stabilizers), pH adjusting agents, thickeners and chelating agents.

The buffers may be selected from but not limited by the group comprising a phosphate buffer, a borate buffer, a citrate buffer, a tartrate buffer, an acetate buffer (for example, sodium acetate) and an amino acid.

The isotonizing agents may be selected from but not limited by the group comprising sugars such as sorbitol, glucose and mannitol, polyhydric alcohols such as glycerin, polyethylene glycol and polypropylene glycol, and salts such as sodium chloride.

The preservatives may be selected from but not limited by the group comprising benzalkonium chloride, benzethonium chloride, alkyl paraoxybenzoates such as methyl paraoxybenzoate and ethyl paraoxybenzoate, benzyl alcohol, phenethyl alcohol, sorbic acid and salts thereof, thimerosal and chlorobutanol.

The solubilizers (stabilizers) may be selected from but not limited by the group comprising cyclodextrin and derivatives thereof, water-soluble polymers such as poly(vinylpyrrolidone), and surfactants such as polysorbate 80 (trade name: Tween 80).

The pH adjusting agents may be selected from but not limited by the group comprising hydrochloric acid, acetic acid, phosphoric acid, sodium hydroxide, potassium hydroxide and ammonium hydroxide.

The thickeners may be selected from but not limited by the group comprising hydroxyethylcellulose, hydroxypropylcellulose, methylcellulose, hydroxypropylmethylcellulose and carboxymethylcellulose and salts thereof.

The chelating agents may be selected from but not limited by the group comprising sodium edetate, sodium citrate and sodium condensed phosphate.

When the pharmaceutical composition of the present invention for treating dry eye is prepared into an ophthalmic ointment, a base compound must be present. The base of the ophthalmic ointment may be selected from but not limited by the group comprising purified lanolin, VASELINE®, plastibase, liquid paraffin and polyethylene glycol.

Alternatively, the composition of the invention can be formulated for oral administration using pharmaceutically acceptable tableting excipients including lactose, microcrystalline cellulose, corn starch, stearic acid, or the like, can be used. Oral administration can also comprise a liquid composition formulated in water, glycols, oils, alcohols or the like.

Coadministration

When the methods of the invention include coadministration, coadministration refers to administration of a first amount of a β-turn peptidomimetic cyclic compound or a pharmaceutically acceptable salt thereof and a second amount of at least one agent selected from the group consisting of anti-inflammatory agents (e.g., RESTASIS® (Allergan)), mucin stimulants (e.g., Diquafasol (Inspire Pharmaceuticals) 15-(S)-HETE (Alcon), rebamipide (Otsuka) and ecabet (ISTA)), hormonal agents and lacrimal gland stimulants (e.g., androgen tears (Allergan)) and artificial tears, wherein the first and second amounts together comprise an effective amount to treat dry eye in a subject in need of treatment. Coadministration encompasses administration of the first and second amounts of the compounds of the coadministration in an essentially simultaneous manner, such as in a single pharmaceutical composition, or in multiple pharmaceutical compositions. In addition, such coadministration also encompasses use of each compound in a sequential manner in either order. When coadministration involves the separate administration of the first amount of the β-turn peptidomimetic cyclic compound or a pharmaceutically acceptable salt thereof and a second amount of at least one agent selected from the group consisting of anti-inflammatory agents (such as, for example, RESTASIS® (Allergan)), mucin stimulants (such as, for example, Diquafasol (Inspire Pharmaceuticals) 15-(S)-HETE (Alcon), rebamipide (Otsuka) and ecabet (ISTA)), hormonal agents and lacrimal gland stimulants (such as, for example, androgen tears (Allergan)) and artificial tears, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile.

Dosing

An effective amount of a β-turn peptidomimetic cyclic compound will depend on the age, sex and weight of the patient, the current medical condition of the patient and the nature of the dry eye disease being treated. The skilled artisan will be able to determine appropriate dosages depending on these and other factors. For example, when the pharmaceutical composition of the present invention is used as an ophthalmic solution for treating dry eye, in a subject in need thereof, it is desirable that an aqueous solution eye drop contain an active ingredient of a compound of the present invention in an amount of approximately 0.001 to 2.5 (w/v) %, such as from 0.02 to 2.0 (w/v), for example from about 0.03 to 1.5 (w/v) %, for example from about 0.05 to 1.0 (w/v) %. As used herein, weight/volume (w/v) means specific mass of solute in a specific final volume (e.g., g/ml). When administered, the compounds and compositions of this invention can be given once daily or with multiple daily doses such as twice per day, three times per day and four times per day. In a particularly preferred embodiment, the compound and compositions of the present invention can be given in a dose of one to five drops, for example, one drop, two drops, three drops, four drops or five drops.

When the pharmaceutical composition of the present invention is used as an ocular ointment, it is desirable that an ocular ointment contain an active ingredient of a compound of the present invention in an amount of approximately 0.001 to 2.5 (w/w) %, such as from 0.02 to 2.0 (w/w), for example from about 0.03 to 1.5 (w/w) %, for example from about 0.05 to 1.0 (w/w) %. As used herein, weight/weight (w/w) means weight of solute in final weight of the solution, e.g., g/g. When administered, the compounds and compositions of this invention maybe given once daily or with multiple daily doses such as twice per day, three times per day and four times per day.

A description of example embodiments of the invention follows.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

EXEMPLIFICATION

Example 1

Effect of β-Turn Peptidomimetic Cyclic Compounds on Glycoconjugate Secretion from Rat Conjunctival Goblet Cells Animals:

The rat inferior conjunctival tissue of Male Sprague-Dawley rats (n=4) weighing between 250 and 300 g was harvested.

Cell Culture:

Similar to the cell culture and assay procedures described in Rios, J. D., et al., "Role of Neurotrophins and Neurotrophin Receptors in Rat Conjunctival Goblet Cell Secretion and Proliferation, *Ophthalmology & Visual Science*, 48: 1543-1551 (2007), explant cultures were established from rat inferior conjunctival tissue. Cells derived from the explants were grown in RPMI 1640 supplemented with 10% fetal bovine serum (FBS) and penicillin (100 U/mL)/streptomycin (100 µg/mL) at 37° C. in a humidified 5% $CO_2$-atmosphere for seventy-two hours. Contaminating nongoblet cells were removed by scraping them from the plate. During this time, goblet cells migrated from the pieces and began to proliferate. After one week, the goblet cells were trypsinized and plated in twenty-four well culture plates with RPMI-1640 media supplemented with 10% FBS.

Measurement of Glycoconjugate Secretion:

To measure glycoconjugate secretion, the conjunctival goblet cells were grown to confluence and were serum deprived for two hours before addition of nerve growth factor (NGF), carbachol (Cch), compound D3, compound 3Aa and compound 3Ak for two hours. Compounds D3, 3Aa and 3Ak were administered at concentrations of 30 µm (micromolar), 10 µM, 1 µM and 0.3 µM. The vehicle used to dissolve the compounds, dimethyl sulfoxide (DMSO) was also included. DMSO was used as the basal control for the 30 µM concentration of compound, which was at 0.1% (v/v). The cholinergic agonist carbachol (Cch), added at 100 µM (micromolar), was a positive control for glycoconjugate secretion. The amount of glycoconjugate secreted into the media was measured by enzyme-linked lectin assay (ELLA). The media were collected and analyzed for amount of the lectin-detectable glycoconjugates, including mucins. The amount of secretion was measured by using the lectin UEA-I which is specific for rat conjunctival goblet cell mucins. Biotinylated UEA-I lectin and alkaline phosphatase-labeled streptavidin were used as described in Rios, J. D., et al., "Role of Neurotrophins and Neurotrophin Receptors in Rat Conjunctival Goblet Cell Secretion and Proliferation, *Ophthalmology & Visual Science,* 48: 1543-1551 (2007), the entire content of which is incorporated herein by reference. The cells were removed and sonicated, and the cell homogenate was analyzed for the total amount of protein by using the Bradford protein assay. This assay revealed that there were equal amounts of protein in each well. Glycoconjugate secretion was expressed as the increase (x-fold) over basal.

Figure 4:
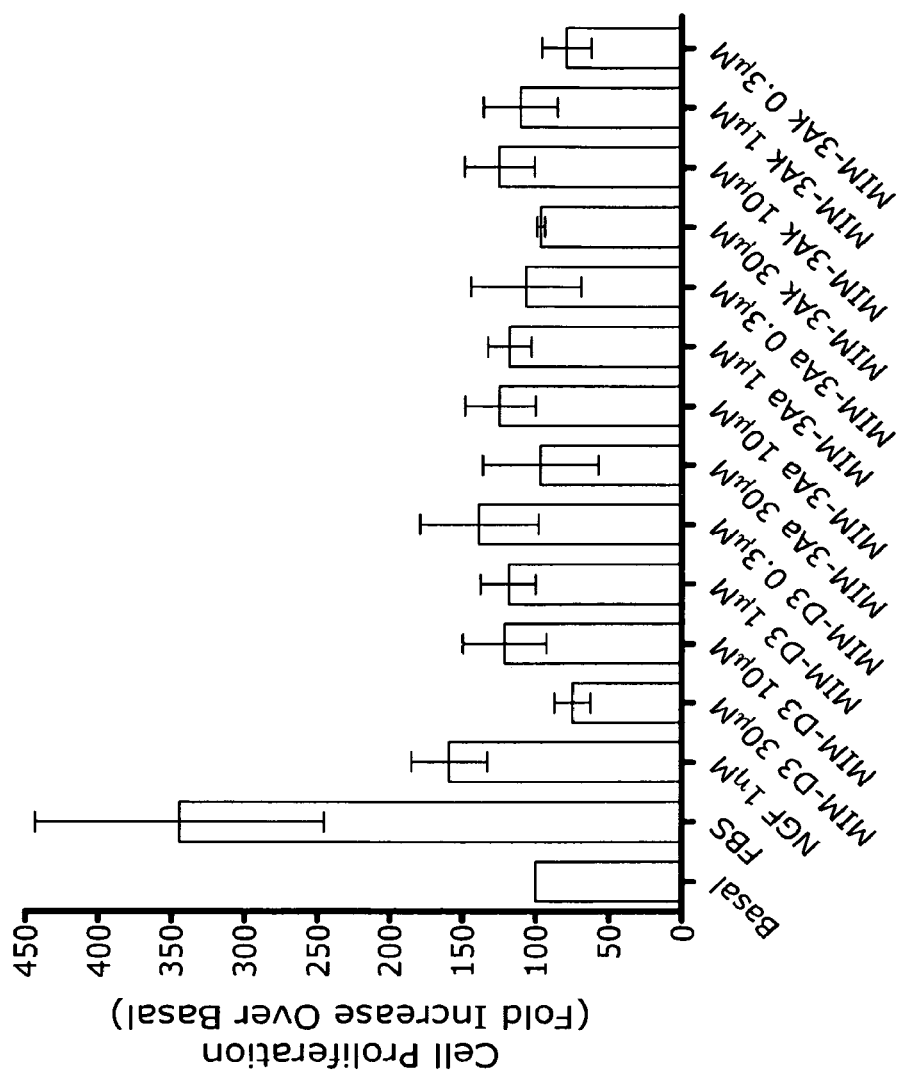
FIG. 4 is a bar graph of data from experiments in conjunctival goblet cells of rats (Rats 1-3). The Y axis represents cell proliferation fold increase above basal. The X axis represents fetal bovine serum (FBS), nerve growth factor (NGF) 1 nM, compound D3, compound 3Aa and compound 3Ak at doses of 30 µM (micromolar), 10 µM, 1 µM and 0.3 µM.

Measurement of Cell Proliferation:

Conjunctival goblet cells were grown to subconfluence in 24-well culture plates and then serum deprived for twenty-four hours. Cells were incubated, with or without increasing concentrations of compound D3, compound 3Aa and compound 3Ak in serum-free RPMI supplemented with 0.5% BSA as a protein source, for twenty-four hours (FIG. 4). Compounds D3, 3Aa and 3Ak were administered at concentrations of 30 µM (micromolar), 10 µM, 1 µM and 0.3 µM. RPMI supplemented with 10% FBS was used as the positive control in cell proliferation studies. CGC proliferation was determined with a colorimetric nonradioactive, WST-8 proliferation assay that measures the number of cells. This procedure employs the 2-(2-methoxy-4-nitrophenyl)-3-(4-nitrophenyl)-5-(2,4-disulfophenyl)-2H-tetrazolium, monosodium salt (WST-8), which is cleaved by viable, growing mitochondria to form a dark blue formazan product that is detected by a fluorescence ELISA reader (Bio-Tek, Winooski, Vt.) at 460 nm.

Data Presentation:

Data for CGC glycoconjugate secretion and proliferation were expressed as the increase (x-fold) above basal value, which was standardized to 1.0. For example, for the 0.3 µM (micromolar), 1 µM and 10 µM doses, the CGC glycoconjugate secretion and proliferation were expressed as test compound over untreated cells. For the 30 µM dose, the CGC glycoconjugate secretion and proliferation were expressed as test compound over DMSO untreated cells. Results are expressed as the mean±sem.

Figure 3:
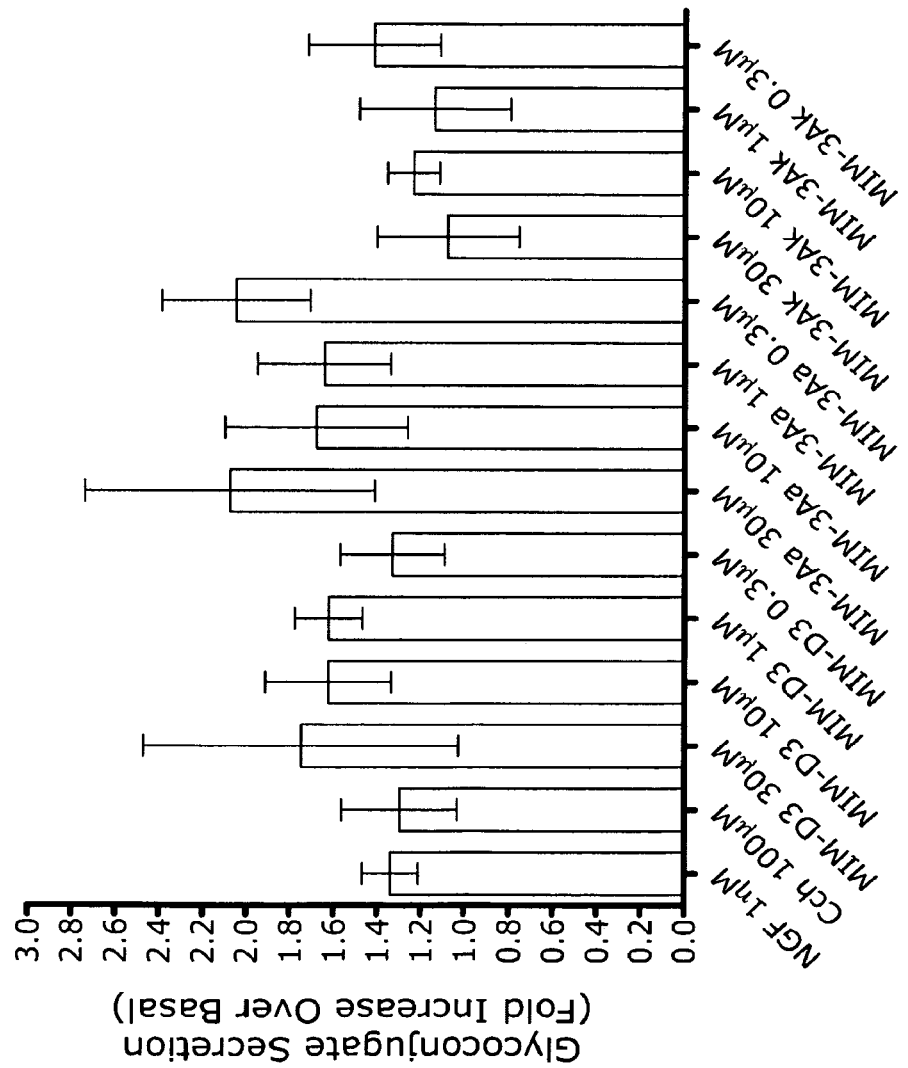
FIG. 3 is a bar graph of data from experiments in conjunctival goblet cells of rats (Rats 1-4). The Y axis represents glycoconjugate secretion fold increase above basal. The X axis represents nerve growth factor (NGF), carbachol (CCh), compound D3, compound 3Aa and compound 3Ak at doses of 30 µM (micromolar), 10 µM and 0.3 µM.

Results:

The results for the glycoconjugate secretion are shown in FIGS. 2 and 3. NGF increased CGC glycoconjugate secretion 1.3±0.1-fold above basal. Cch, a known goblet cell agonist, increased CGC glycoconjugate secretion 1.3±0.3-fold above basal.

Compound D3 increased CGC glycoconjugate secretion and indicated a concentration-dependent trend. Compound D3 increased CGC gycoconjugate secretion as follows: 1.7±0.7-fold above basal (30 µM), 1.6±0.3-fold above basal (10 µM), 1.6±0.2-fold above basal (1 µM) and 1.3±0.2-fold above basal (0.3 µM).

Compound 3Aa increased CGC glycoconjugate secretion as follows: 2.1±0.7-fold above basal (30 µM), 1.7±0.4-fold above basal (10 µM), 1.6±0.3-fold above basal (1 µM), and 2.1±0.3-fold above basal (0.3 µM). Compound 3Aa showed a greater increase in CGC glycoconjugate secretion as compared to NGF and Cch.

Compound 3Ak did not show as robust an effect as compounds D3 and 3Aa but did demonstrate activity. The results for compound 3Ak CGC glycoconjugate secretion are as follows: 1.1±0.3-fold above basal (30 µM), 1.2±0.1-fold above basal (10 µM), 1.1±0.3-fold above basal (1 µM) and 1.4±0.3-fold above basal (0.3 µM).

The results for the cell proliferation are shown in FIG. 4. In the proliferation assay, none of the compounds at any concentration tested induced goblet cell proliferation after 24 hours of incubation. As controls, fetal bovine serum 10% (FBS) increased CGC proliferation 3.4±1.0-fold above basal, and NGF increased CGC proliferation 1.6±0.3-fold above basal.

The β-turn peptidomimetic cyclic compounds tested stimulated mucin secretion, and, therefore, can be useful in the method of treating dry eye disease in a subject in need thereof.

Example 2

Effect of Compound D3 in Glycoconjugate Secretion, Proliferation and Signal Transduction in Rat Conjunctival Goblet Cells The purpose of this study was to determine the efficacy of compound D3 in glycoconjugate secretion and proliferation of cultured rat conjunctival goblet cells, and to investigate the signal transduction pathway compound D3 used to stimulate secretion.

Animals:

Six to eight-week-old male Sprague-Dawley rats were obtained from Charles River (Wilmington, Mass.). Animals were housed 2 per cage under constant light conditions (12-h light/12-h dark cycle), room temperature (22±1° C.) and relative humidity (40-70%). All procedures in this study complied with McGill University's animal welfare policies and were approved by the Lady Davis Research Institute (LDI) Animal Care and Use Committee. The standards for animal care and use conform with or exceed those defined in the Canadian Council on Animal Care (CCAC).

Isolation of Conjunctival Tissue:

Animals were anaesthetized before euthanasia in an Isofluorane 99.9% USB (Abraxis Bioscience, Richmond Hill, Ont) chamber. Animals were euthanized by lethal dose of sodium pentobarbital 2 mL/0.4 kg or 300 mg/kg (Ceva Sante Animale, Libourne, France). Conjunctival tissue, more specifically the nictitating membranes and formix, were excised and immediately placed into Hanks" balanced salt solution containing 3× penicillin-streptomycin (300 ug/mL). The formix was identified as the band running along the most posterior part of the fold at the junction of the bulbar and palpebral conjunctiva. The lower, nasal portion of the formix was grasped and lifted, and it was cut from the conjunctiva.

Culture of Conjunctival Goblet Cells:

RPMI-1640 culture medium, fetal bovine serum (FBS), penicillin-streptomycin, and Hank's balanced salt solution were obtained from Wisent (St. Bruno, Quebec). L-glutamine and 0.05% trypsin-EDTA were from Gibco (Grand Island, N.Y.). Tissue culture flasks and culture dishes were from Corning (Lowell, Mass.) and Laboratory Tek chamber slides were from Nunc (Rochester, N.Y.).

The culturing of conjunctival goblet cells from explant cultures was as previously described in Shatos, M. et al., "Isolation, Characterization, and Propagation of Rat Conjunctival Goblet Cells In Vitro," IOVS 42:1455-1464 (2001), the entire content of which is incorporated herein by reference. The tissue was finely minced and individual pieces were anchored onto scored 6-well cultures dishes in 0.5 mL of complete RPMI-1640 (supplemented with 10% FBS, 2 mM glutamine and 100 µg/mL penicillin-streptomycin) and incubated at 37° C. in a humidified 5% $CO_2$-atmosphere. Explant cultures were refed every 2 days. Within a few days, goblet cells migrated from the pieces and began to proliferate. After approximately one week, the tissue plugs were removed and the goblet cells were allowed to grow to confluence. Cells were passaged once by trypsinization of adherent cells with 0.05% trypsin-0.53 mM EDTA (pH 7.4), and plated in 8-well Laboratory Tek chamber slides (histochemistry) or in 96 well (proliferation), 24 well (secretion), or 6 well (western blots) culture plates with complete RPMI-1640 media.

Histochemistry:

Cells were fixed and processed for Periodic Acid-Schiff (PAS) staining and counterstained with Hematoxylin Solution, Gill No. 3 kit (Sigma Aldrich, St. Louis, Mo.) according to the manufacturers instructions. All procedures were performed at room temperature. Briefly, cells were fixed for 15 minutes in methanol. Slides were rinsed in tap water for 1 minute, stained in Periodic Acid Solution for 5 minutes, rinsed 5 times in distilled water, immersed in Schiff's reagent for 15 minutes, washed in tap water for 5 minutes, stained in Hematoxylin Solution for 90 seconds, rinsed in tap water for 15-30 seconds, air dried and mounted in Vectamount (Vector Labs, Burlingame, Calif.). Slides were examined and photographed with a Leica DM LB 2 microscope equipped with a Leica DFC480 camera.

Test Articles and Preparation of Solutions:

Compound D3 (Hydrochloride salt, lot number 12-95) manufactured by Mimetogen Pharmaceuticals (Montreal, Quebec, Canada) was dissolved in saline to give a 10 mM stock solution.

NGF (recombinant human) is a 3.16 mg/mL solution in buffer [20 mM sodium acetate, 136 mM sodium chloride, pH 5.5] and stored refrigerated (2-8° C.). The biological activity of this solution was tested for its ability to cause differentiation of PC12 cells at nanomolar concentrations.

Phorbol-12-myristate-13-acetate (PMA) (Sigma, St. Louis, Mo.) was prepared as a 10-mg/mL (16.2 mM) stock solution in DMSO.

Prior to the experiments, test articles were diluted in media for final concentrations as described in the figures. Basal cultures were incubated with the saline vehicle control.

Growth, Morphology and Characterization of Cultured Goblet Cells

Figure 5:
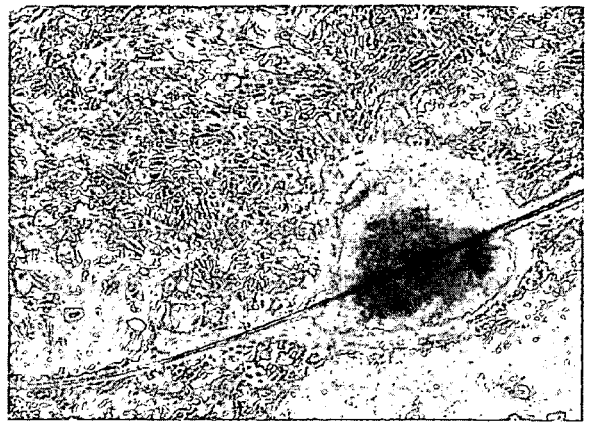
FIGS. 5A-C shows growth morphology of goblet cells in culture.
Figure 5:
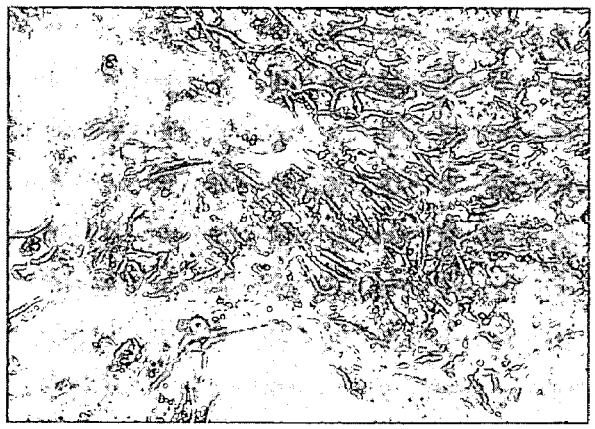
Figure 5:
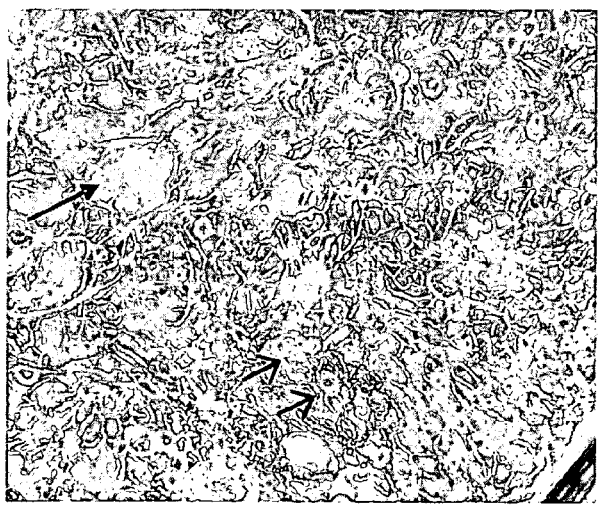

As early as 2 days after establishment of the tissue plug, cells started to grow out from the tissue which continue to grow so that by day 9 adherent cells are visible all around the tissue (FIG. 5A). On higher magnification, single cells adhering to the tissue culture well, exhibit cobblestone morphology and contain tiny translucent droplets in cytoplasmic vesicles (FIG. 5B). Often as cells proliferated in culture, tiny droplets were observed to form on the surface of the goblet cells, suggestive of a mucus-like secretory product (FIG. 5C, open arrows). As these droplet-containing cells grew in culture, the droplets merged into pools, which increased in size and number (FIG. 5C, closed arrow). The results are similar to previously published results (Shatos, M. et al., "Isolation, Characterization, and Propagation of Rat Conjunctival Goblet Cells In Vitro," IOVS 42:1455-1464 (2001), the entire content of which is incorporated herein by reference).

Figure 6:
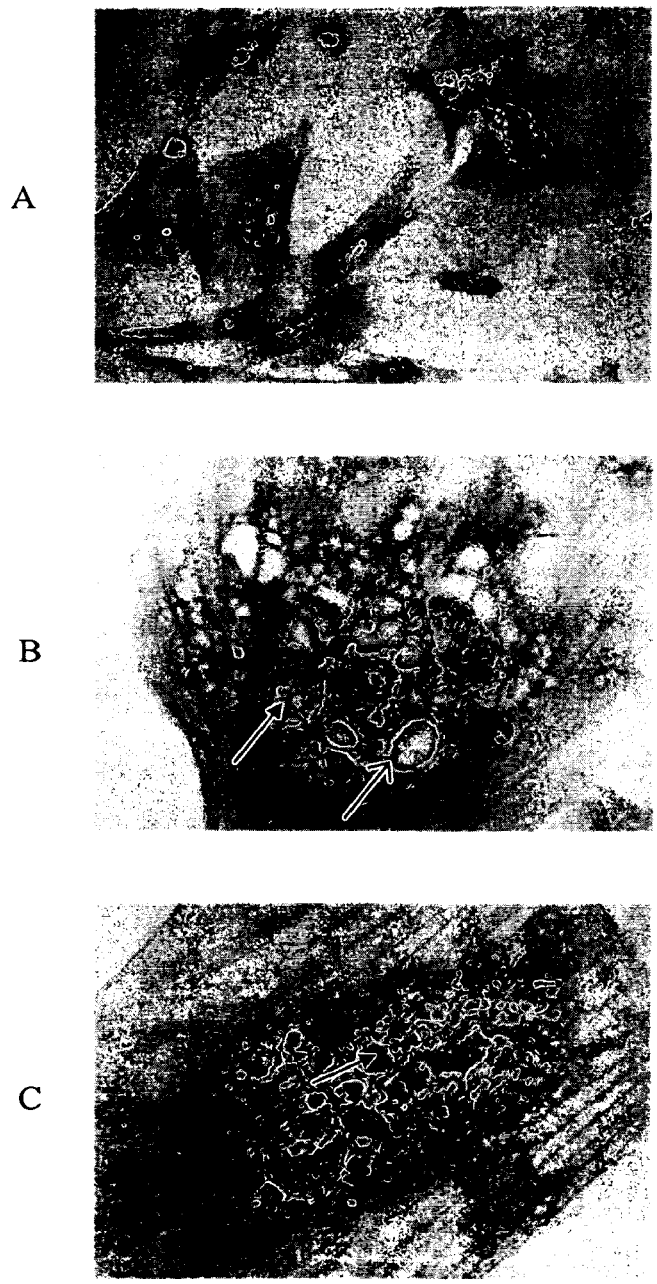
FIGS. 6A-C shows histochemical analysis of primary cultures of goblet cells to Periodic Acid-Schiff (PAS) staining.

It was determined that these cells have positive reactivity to PAS, indicating that these cells were associated with a neutral type of mucin secretion product (FIG. 6A). Upon higher magnification (100×), many cytoplasmic peri-nuclear vesicles were observed (FIG. 6B, open arrow). On examination, several of these vesicles stained intensely with PAS, indicating the presence of neutral (pink to red) glycoconjugates within secretory granules (FIGS. 6B and C, closed arrows). The cells are counterstained blue with Heamatoxylin/Eosin stain.

Endpoints and Results:

As discussed in detail below, compound D3 increased mucin secretion in conjunctival goblet cells with the greatest increase seen at the 2 µM dose. In addition, compound D3 at concentrations up to 100 µM did not stimulate goblet cell proliferation by day 4, with no differences among the doses. Lastly, treatment of conjunctival goblet cells for five minutes with compound D3 increased mitogen-activated protein kinase (MAPK) phosphorylation.

Glycoconjugate Secretion:

To measure cell secretion, goblet cells were grown to confluence and then serum depleted for 2 hours prior to stimulation. Cells were incubated with compound D3 at 2, 10, and 50 µM, NGF at 0.1, 1 and 10 nM, and PMA at 0.1, 1, and 10 nM in serum-free RPMI for 2 hours. Goblet cell secretion was measured using an enzyme-linked lectin assay (ELLA). Briefly, an aliquot of the cell culture supernatant was transferred to a 96-well polystyrene microtiter plate in triplicate (Corning Life Sciences #2592, Fisher Scientific, Nepean, Ont). A dilution series of bovine submaxillary mucin (BSM) (Sigma, St. Louis, Mo.) was included on each plate as the standard (standard curve data and data showing that detection of BSM is linear between 0.003 and 0.1 µg not shown). The plates were coated by evaporation at 37° C. overnight. After, the plates were washed three times with wash buffer [PBS containing 0.3% BSA, 0.05% Tween-20] then blocked for nonspecific binding with PBS containing 3% BSA and 0.05% Tween-20 at 37° C. for 1 hour. The wells were rinsed three times in wash buffer, and then incubated in 2 µg/mL biotinylated UEA-1 diluted in wash buffer (Vector Labs, Burlingame, Calif.) at 37° C. for 1 hour. The wells were rinsed three times in wash buffer, and then incubated in 1 µg/mL HRP-conjugated neutravidin diluted in wash buffer (Pierce, Rockford, Ill.) at 37° C. for 1 hour. After the wells were rinsed three times in wash buffer, the color development was performed with TMB (Promega, Madison, Wis.) and stopped with 0.5N Sulfuric acid. The absorbance was read at 450 nm on a Benchmark Plus (Biorad). The goblet cells remaining in the culture wells were either scraped in RIPA buffer [1% TritonX-100, 20 mM Tris-HCl pH 7.5, 150 mM NaCl, 1.5 mM $MgCl_2$, 1% Na deoxycholate, 1 mM EGTA, 1 mM EDTA, 0.1% SDS, 10% glycerol, 1 mM Na vanadate, 10 mM Na fluoride, 10 mM Na pyrophosphate, complete mini EDTA-free protease inhibitors (Roche Applied Science, Indianapolis, Ind.)] or 1M Tris-buffer (pH 7.5), collected and sonicated. The amount of protein in the cell homogenate was analyzed using the Bradford protein assay kit using a dilution series of bovine serum albumin (BSA) as the standard (BioRad, Montreal, PQ). Glycoconjugate secretion was normalized to total protein in the homogenate. Data was then expressed as fold increase above basal.

To determine whether compound D3 stimulates goblet cell mucin secretion, cultured passaged goblet cells were incubated for 2 hours in the presence of compound D3 (2, 10 and 50 µM), or NGF (0.1, 1 and 10 nM, the positive control (Rios, J. et al., "Role of Neurotrophins and Neurotrophin Receptors in Rat Conjunctival Goblet Cell Secretion and Proliferation," IOVS 48:1543-1551 (2007), the entire content of which is incorporated herein by reference) or PMA (0.1, 1 and 10 nM, another positive control (Dant, D. et al., "Regulation of Conjunctival Goblet Cell Secretion by Ca2+ and Protein Kinase," C. Exp Eye Res 71:619-628 (2000), the entire content of which is incorporated herein by reference). An ELLA determined the amount of high molecular weight glycoproteins secreted into the medium using the biotinylated lectin UEA-1 as previously described in Rios, J. et al., "Immunolocalization of Muscarinic and VIP Receptor Subtypes and Their Role in Stimulating Goblet Cell Secretion," IOVS 40:1102-1111 (1999), the entire content of which is incorporated herein by reference). The raw data of mucin secretion from cultured goblet cells from four independent rats are presented in Table 1.

TABLE 1

Raw Data of Goblet Cell Glycoconjugate Secretion

| | Glycoconjugate Secretion ($\mu$g glycoconjugate/mg total protein) | | | | | | | |
|---|---|---|---|---|---|---|---|---|
| | Rat 1 | | Rat 2 | | Rat 3 | Rat 4 | | Mean ± |
| Sample | Plate 1 | Plate 2 | Plate 1 | Plate 2 | Plate 1 | Plate 1 | Plate 2 | SD |
| Basal | 5.1 | 3.9 | 2.0 | 2.3 | 4.9 | 8.6 | 9.9 | 5.7 ± 3.0 |
| NGF (0.1 nM) | 7.6 | | 2.4 | | 4.6 | 10.6 | | 6.3 ± 3.6 |
| NGF (1 nM) | 13.6 | | 1.7 | | 4.9 | 10.8 | | 7.8 ± 5.4 |
| NGF (10 nM)) | 10.4 | 4.4 | 3.6 | 2.7 | 9.7 | 10.2 | | 6.8 ± 3.6 |
| PMA (0.1 nM) | | | | 3.2 | 6.9 | | | 5.1 ± 2.6 |
| PMA (1 nM) | | 4.1 | | 4.1 | | | | 4.1 ± 0 |
| PMA (10 nM) | 11.3 | 3.5 | | 3.0 | 6.1 | | 8.4 | 6.5 ± 3.5 |
| MIM-D3 (2 $\mu$M) | | | | 2.5 | 10.5 | 9.3 | | 7.4 ± 4.3 |
| MIM-D3 (10 $\mu$M) | | | | 2.5 | 5.1 | 11.6 | | 6.4 ± 4.7 |
| MIM-D3 (50 $\mu$M) | | 5.4 | | 3.3 | 5.7 | 9.5 | | 6.0 ± 2.6 |

Figure 7:
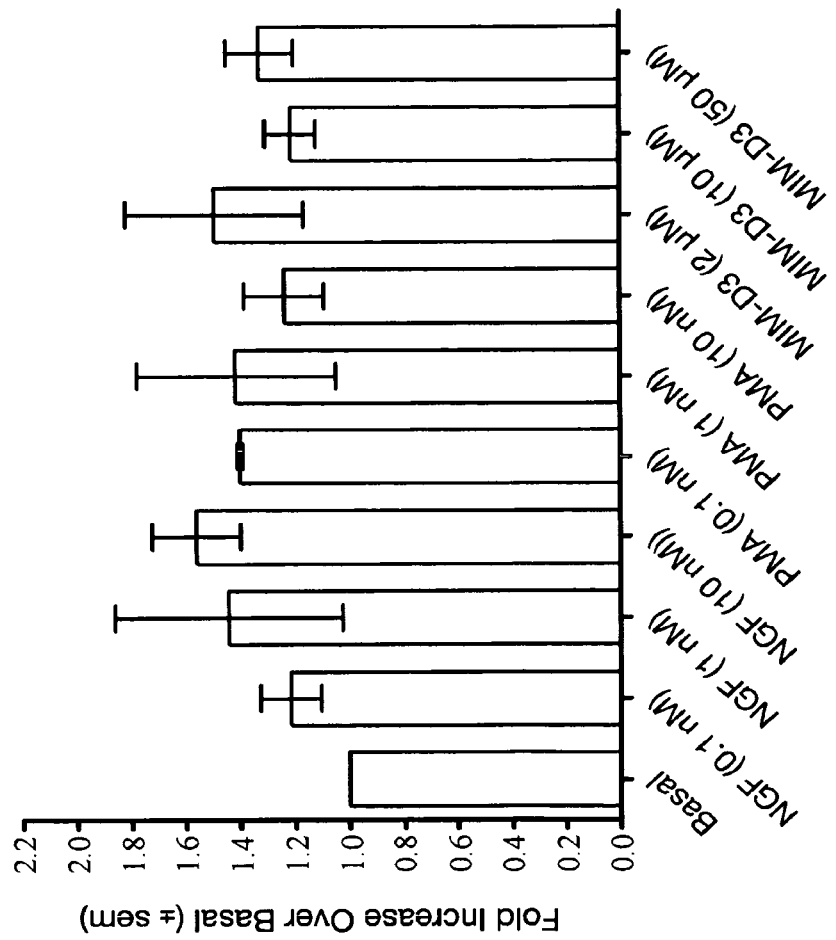
FIG. 7 is a bar graph of the effect of phorbol-12-myristate-13-acetate (PMA) (0.1, 1 and 10 nM), NGF (0.1, 1 and 10 nM) and compound D3 (2, 10 and 50 Mµ) on glycoconjugate secretion in fold increase over basal (±sem). The Y axis represents glycoconjugate secretion fold increase above basal (±sem). The X axis represents basal, NGF (0.1, 1 and 10 nM), PMA (0.1, 1 and 10 nM) and compound D3 (2, 10 and 50 µM).

There was little difference in mucin secretion from rat to rat, with basal secretion ranging between 2.0 and 9.9 $\mu$g glycoconjugate/mg protein. The positive control NGF increased mucin secretion in a dose-dependent manner (up to 1.55±0.18 fold at 10 nM) (Table 2). The other positive control, PMA increased mucin secretion by ~1.4 fold, which was not dose-dependent. Compound D3 increased mucin secretion; the greatest increase was seen at 2 $\mu$M (1.49±0.33 fold). None of the treatments were statistically significant from each other (P=0.7429). A graphical representation of the data is presented in FIG. 7.

TABLE 2

Fold Increases in Glycoconjugate Secretion

| | Glycoconjugate Secretion (Fold increase above basal) | | | | |
|---|---|---|---|---|---|
| Sample | Rat 1 | Rat 2 | Rat 3 | Rat 4 | Mean ± sem |
| Basal | 1.00 | 1.00 | 1.00 | 1.00 | 1.00 ± 0.00 |
| NGF (0.1 nM) | 1.49 | 1.20 | 0.94 | 1.24 | 1.22 ± 0.11 |
| NGF (1 nM) | 2.67 | 0.85 | 1.00 | 1.26 | 1.44 ± 0.42 |
| NGF (10 nM)) | 1.58 | 1.49 | 1.98 | 1.19 | 1.55 ± 0.18 |
| PMA (0.1 nM) | | 1.39 | 1.41 | | 1.40 ± 0.01 |
| PMA (1 nM) | 1.05 | 1.78 | | | 1.42 ± 0.37 |
| PMA (10 nM) | 1.56 | 1.30 | 1.24 | 0.85 | 1.30 ± 0.25 |
| MIM-D3 (2 $\mu$M) | | 1.25 | 2.14 | 1.09 | 1.49 ± 0.33 |
| MIM-D3 (10 $\mu$M) | | 1.25 | 1.04 | 1.35 | 1.21 ± 0.09 |
| MIM-D3 (50 $\mu$M) | 1.38 | 1.65 | 1.16 | 1.11 | 1.33 ± 0.12 |

Cell Proliferation:

Cell proliferation was measured using Alamar Blue from Biosource (Invitrogen Corporation, Carlsbad, Calif.) according to the manufacture's protocol. Cultured goblet cells from two rats were serum starved in serum-free RPMI supplemented with 0.5% BSA for 24 hrs prior to the addition of FBS (10%, the positive control), NGF (10 $\mu$M to 10 nM), compound D3 (0.1 to 100 $\mu$M) or NGF (10 $\mu$M to 10 nM) in the presence of 10 or 100 $\mu$M MIM-D3, and further incubated at 37° C. in a humidified 5% $CO_2$—atmosphere. After 24 hours, 10% Alamar Blue was added for 6 hours and the absorbance was read at 570 and 600 nm on a Benchmark Plus (Biorad). The percentage of Alamar Blue reduction was calculated according to the manufacture's instructions. The Alamar Blue containing plates were further incubated at 37° C. for 48, 72 and 96 hours, and the plates reread each day. Goblet cell proliferation was measured in the presence of 10% FBS for up to four days.

Figure 8:
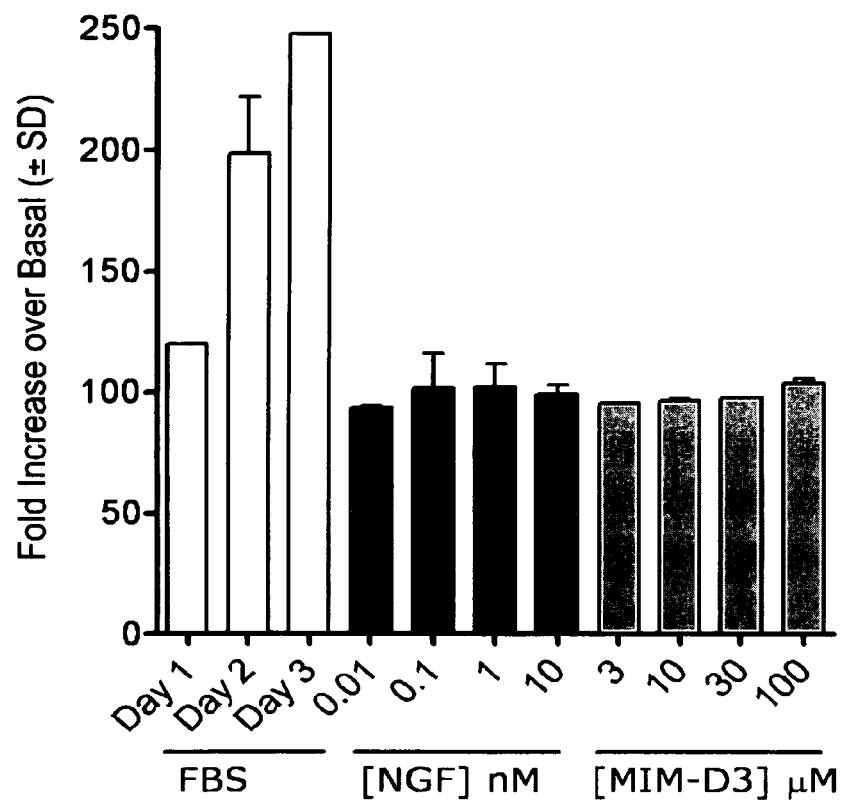
FIG. 8 is a bar graph of the effect of NGF (0.01, 0.1, 1 and 10 nM) and compound D3 (3, 10, 30 and 100 µM) on goblet cell proliferation. The Y axis represents cell proliferation fold increase over basal (±SD). The X axis represents FBS, NGF (0.01, 0.1, 1 and 10 nM), and compound D3 (3, 10, 30, and 100 µM).

A statistically significant increase in proliferation was obtained over time with 10% FBS (247±2 fold at day 3, P<0.0001). After three days of incubation with 10% FBS the percent reduction of Alamar Blue decreased due to high cell numbers or extended incubation times. To determine whether compound D3 and NGF stimulates goblet cell proliferation, goblet cells were incubated in serum-free media in the presence of increasing concentrations of compound D3 (FIG. 8) or NGF for up to four days. NGF at all concentrations did not increase proliferation up to day four. Compound D3 at concentrations up to 100 $\mu$M did not stimulate goblet cell proliferation by day four (concentrations less than 3 $\mu$M are not shown) with no differences among the dose response (P=0.1098). Combination of NGF with 10 $\mu$M or 100 $\mu$M compound D3 had no effect on proliferation (data not shown).

MAPK:

The activation of p42/44 MAPK was examined using Western blot techniques. Goblet cells were serum starved in serum-free RPMI for 4-6 hrs prior to the addition of PMA (100 nM), NGF (1 or 10 nM), or MIM-D3 (10 or 50 $\mu$M) for 5 minutes at 37° C. After, cells were rinsed once in cold PBS, scraped in 100 $\mu$L of 1×SDS-PAGE sample buffer [62.5 mM Tris-HCl pH 6.8, 10% glycerol, 2% SDS, 5% $\beta$-mercaptoethanol, 0.02 mg/mL bromophenol blue] and sonicated for 20 minutes. The homogenates were centrifuged at 14,900 g for 15 min at 4° C. Proteins in a 30-4 aliquot of the supernatant were separated by SDS-PAGE (8% acrylamide gels) and transferred to nitrocellulose membranes. The membranes were blocked for 2 hours in 5% non-fat dried milk in buffer containing 20 mM Tris-HCl, pH 8.0, 150 mM NaCl, and 0.01% Tween-20 (TBST). The blots were then probed with an antibody directed against the phosphorylated form of MAPK1/2 (Calbiochem, San Diego, Calif.) at 0.1 $\mu$g/mL in TBST containing 5% BSA overnight at 4° C., followed by a 1 hour incubation in HRP-conjugated secondary anti-mouse antibody (Sigma, St. Louis, Mo.) at room temperature in TBST containing 5% non-fat dried milk. Immunoreactive bands were visualized using the enhanced chemiluminescence method (Perkin Elmer, Waltham, Mass.). The blots were stripped at 55° C. for 30 minutes in stripping buffer [62.5 mM Tris-HCl pH 6.8, 2% SDS, 0.1M β-mercaptoethanol] followed by re-probing with an antibody directed against actin (1:5000 dilution, Sigma, St. Louis, Mo.) in TBST containing 5% non-fat dried milk and incubation in HRP-conjugated secondary anti-rabbit antibody. The immunoreactive bands were digitally scanned on an EPSON scanner and analyzed using NIH ImageJ v1.38x. The amount of phosphorylated MAPK in each sample was standardized to the amount of total actin protein in the sample.

Figure 9:
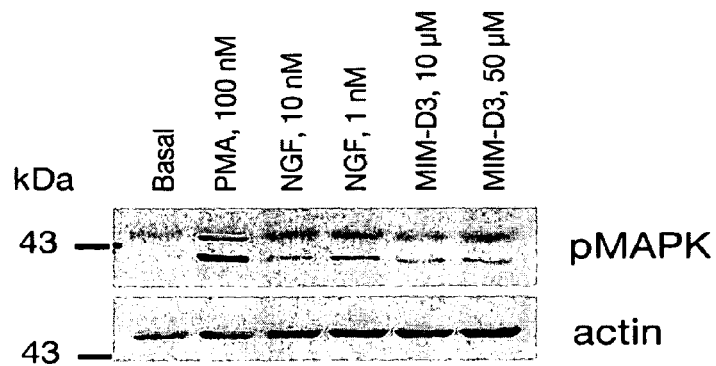
FIG. 9 shows a western blot of the effect of PMA (100 nM), NGF (1 nM and 10 nM) and compound D3 (10 µM and 50 µM) on mitogen-activated protein kinase (MAPK) activity.
Figure 10:
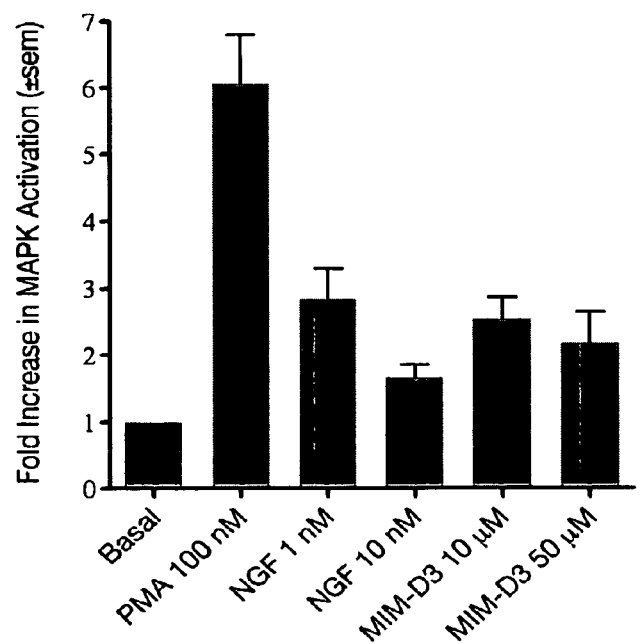
FIG. 10 is a bar graph of the quantification of MAPK activation relative to total actin protein for basal, PMA (100 nM), NGF (1 nM and 10 nM) and compound D3 (10 µM and 50 µM). The Y axis represents fold increase in MAPK activation (±sem). The X axis represents basal, PMA (100 nM), NGF (1 and 10 nM) and compound D3 (10 and 50 µM).

To determine if compound D3 and NGF induced glycoconjugates secretion via activation of the MAPK pathway, cultured goblet cells from 3 independent rats were stimulated by 10 and 50 µM compound D3, 1 and 10 nM NGF or PMA (100 nM, the positive control) for 5 minutes and MAPK activity was measured by western blot analysis. A representative western blot from 3 independent rat goblet cell cultures is shown in FIG. 9, and the quantification is shown in FIG. 10. There was a statistically significant effect of treatment on MAPK activation ($P<0.0001$). Compound D3 increased MAPK activity above basal by $2.5\pm0.3$ fold at 10 µM and $2.2\pm0.5$ fold at 50 µM and NGF increased MAPK activity by $2.8\pm0.5$ at 1 nM ($P<0.05$) and $1.7\pm0.2$ at 10 nM. The positive control PMA statistically significantly increased MAPK activity $6.1\pm0.7$ fold ($P<0.01$).

Data Presentation and Statistical Analysis:

Data are expressed as the increase (x-fold) above basal value, which was standardized to 1.0. Results are expressed as the mean±SEM. Data are analyzed by one-way ANOVA using GraphPad Prism v4.0c (GraphPad Software Inc., La Jolla, Calif.). $P<0.05$ is considered statistically significant. For comparison to basal control adjustment with Dunnett's test was used.

Example 3

Scopolamine Induced Dry Eye Model (Compound D3)

The purpose of this study was to use the scopolamine model of dry eye to study the efficacy of compound D3. The scopolamine model was chosen based on earlier research comparing a controlled environment chamber (CEC) to the scopolamine model of dry eye.

Animals:

Male Sprague-Dawley rats weighing between 300 g and 350 g were obtained from Charles River (Wilmington, Mass.). Animals were housed in animal quarters under constant room temperature ($22\pm1°$ C.), light conditions (12-h light/12-h dark cycle), and humidity (40-60%). Animals were anaesthetized before the surgical experiment and clinical examination with isofluorane.

Induction of Dry Eye by Cholinergic Blockade:

Dry eye was induced using scopolamine (Sigma-Aldrich, St. Louis, Mo.), which was continuously and systemically delivered to the animals via an osmotic pump (2ML4 Alzet®; CedarLane, Burlington, Ontario) filled with scopolamine and implanted subcutaneously in the mid dorsal area between the scapulae. The wound was closed with 2-3 wound clips. After the surgery and again the next day, the animals were subcutaneously injected with Carprofen (0.5 mg/100 g) a non-steroidal anti-inflammatory drug and potent, long-acting analgesic in rodents. Animals were anaesthetized before the surgical pump implantation and before all clinical endpoint testing in an Isofluorane 99.9% USP (Abraxis Bioscience, Richmond Hill, Ontario) chamber. Scopolamine was delivered at 12.5 mg/day and, for technical reasons, the data was evaluated at day 14.

The sterile solution of 0.175 g/mL of scopolamine hyrdobromide (Sigma-Aldrich, St. Louis Mo.) was prepared in saline (0.9%) and filtered through a 0.22 um syringe-end filter (Millex-GC, Millipore Corp., Bedford, Mass.). The 2ML4 Alzet® pumps were filled with 2 mL of 0.175 g/mL scopolamine solution according to the manufacturer's instructions.

Treatment Groups:

The groups of rat eyes tested were as follows:

Group 1: Control rats (n=12 eyes from 6 rats).

Group 2: Rats (n=12 eyes from 6 rats) were induced with dry eye by systemic administration of scopolamine continuously and the measurement of fluorescein staining was taken at day fourteen.

Group 3: Rats (n=14 eyes from 7 rats) were induced with dry eye by systemic administration of scopolamine continuously and treated once topically on day eight with saline.

Group 4: Rats (n=14 eyes from 7 rats) were induced with dry eye by systemic administration of scopolamine continuously and treated once topically on day eight with a 5 µl instillation of 1% (10 mg/mL) of compound D3.

Clinical Endpoints for Dry Eye and Results:

As discussed in detail below, the group treated with topical 1% compound D3 on day eight had a significant reduction ($p<0.0001$) in corneal fluorescein staining, with a mean score of $1.1\pm0.1$ as compared to the saline-treated control on day fourteen, but had no effect on aqueous tear production and aqueous tear turnover as measured at day thirteen as compared to the untreated or scopolamine treated controls.

There were no mortalities, but there were two morbidities (one in Group 2 and one in Group 3) in which the incision wound sites were reopened due to chewing and the pumps exposed. The clinical sign data was excluded for these two animals. Mild to severe ocular irritation was observed in all scopolamine treated animals (Groups 2-4) from day two onward. Most scopolamine treated animals eyes showed conjunctival congestion, swelling and conjunctival bloody discharge. Conjunctival congestion and bloody discharge usually resolved. However, the conjunctival swelling continued throughout the study. Ocular irritation was observed during the dosing of the animals, even under anesthesia.

Pre-treatment, mean body weight was approximately 350 g, and was not statistically different among groups ($P=0.3999$). Mean body weight in the untreated control groups (Group 1) increased to approximately 420 g by Day 14. In the three groups receiving scopolamine (Group 2-Group 4), mean body weight increased to approximately 375 g. There was a statistically significant effect of treatment to decrease body weight starting on Day 7, continuing through Day 14 ($P=0.0042$).

Corneal Staining:

The clinical signs of corneal dryness were evaluated by fluorescein impregnation of the cornea. A drop of a 1% fluorescein sodium (Sigma-Aldrich, St. Louis, Mo.) solution made up in sterile saline was instilled in the conjunctival sac of the anaesthetized animal. The cornea was thereafter observed under blue light using a Portable Slit Lamp ophthalmoscope with blue cobalt filter (Reichert Opthalmic Instruments, Depew, N.Y.) three minutes after fluorescein instillation. For each animal, the punctate fluorescent-positive area of the ocular surface was recorded in a blinded fashion. The score of this test was graded from 0 to 4, where 0=no staining, 1=<25% surface staining, 2=25-50% surface staining, 3=50-75% surface staining and 4=>75% surface staining.

Figure 11:
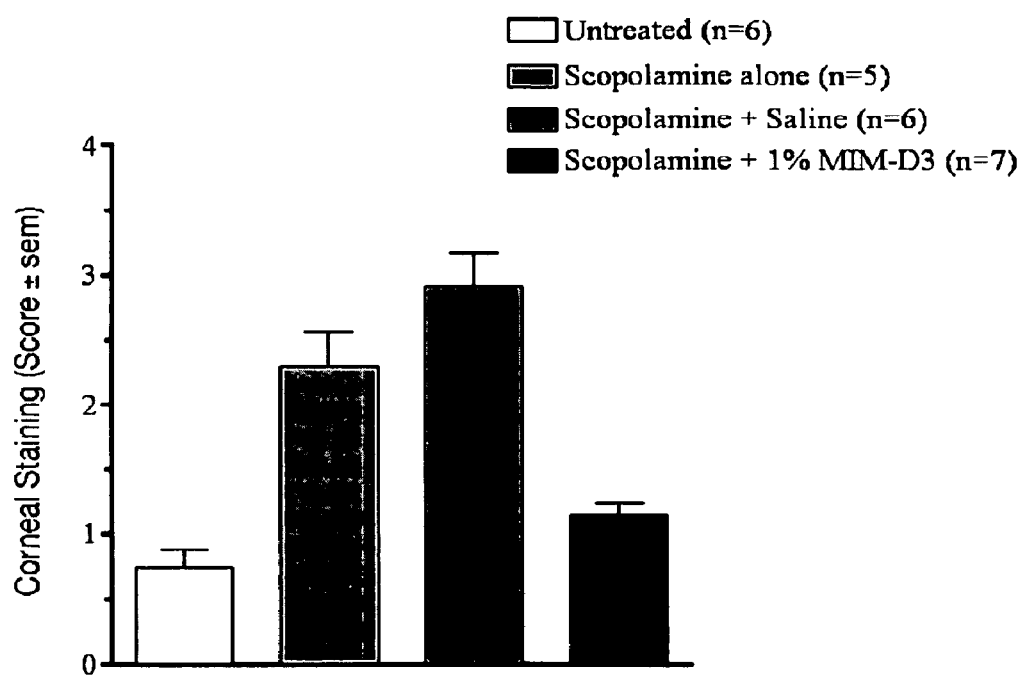
FIG. 11 is a bar graph of fluorescein corneal staining scores (score±sem) from negative control rats (untreated; n=6 rats), rats with dry eye model induced by systemic scopolamine continuously for fourteen days (scopolamine; n=5 rats), rats with dry eye model treated once topically on day eight with saline (scopolamine+saline; n=6 rats), and rats with dry eye model treated once topically on day eight with 50 ug of 1% compound D3 (scopolamine+1% compound D3; n=7 rats) at day 14 post scopolamine implantation.

As shown in FIG. 11, the control group (naïve) showed almost complete absence of corneal fluorescein staining, with a mean score (Score±SD) of 0.8±0.1. The untreated dry eye group (scopolamine alone) showed a significant degree of punctate and diffuse corneal fluorescein staining, with a mean score of 2.3±0.3 on day fourteen post-scopolamine pump implantation. The group treated with topical saline on day eight post-scopolamine pump implantation also showed a significant degree of corneal fluorescein staining on day fourteen, similar to the untreated dry eye group, with a mean score of 2.9±0.3. The group treated with topical 1% compound D3 on day eight had a significant reduction (p<0.0001) in corneal fluorescein staining, with a mean score of 1.1±0.1 as compared to the saline-treated control on day fourteen. In addition, at day fourteen the mean value in the group treated with topical 1% compound D3 (1.1±0.1) was not statistically different from Group 1 (untreated control, 0.8±0.1, p>0.05).

Schirmer Test:

Tear production was measured with Zone-Quick standardized phenol-red threads (FCI Ophthalmics, Marshfield Hills, Mass.) on animals lightly sedated with Isoflurane. The threads were inserted in the lateral lower canthus and left in place for thirty seconds. The length of the stained moistened portion of the thread was measured in millimeters, using the scale provided with the threads to an accuracy of 1 mm. Schirmer testing was routinely combined with tear fluorescein clearance as described in the section below.

Figure 12:
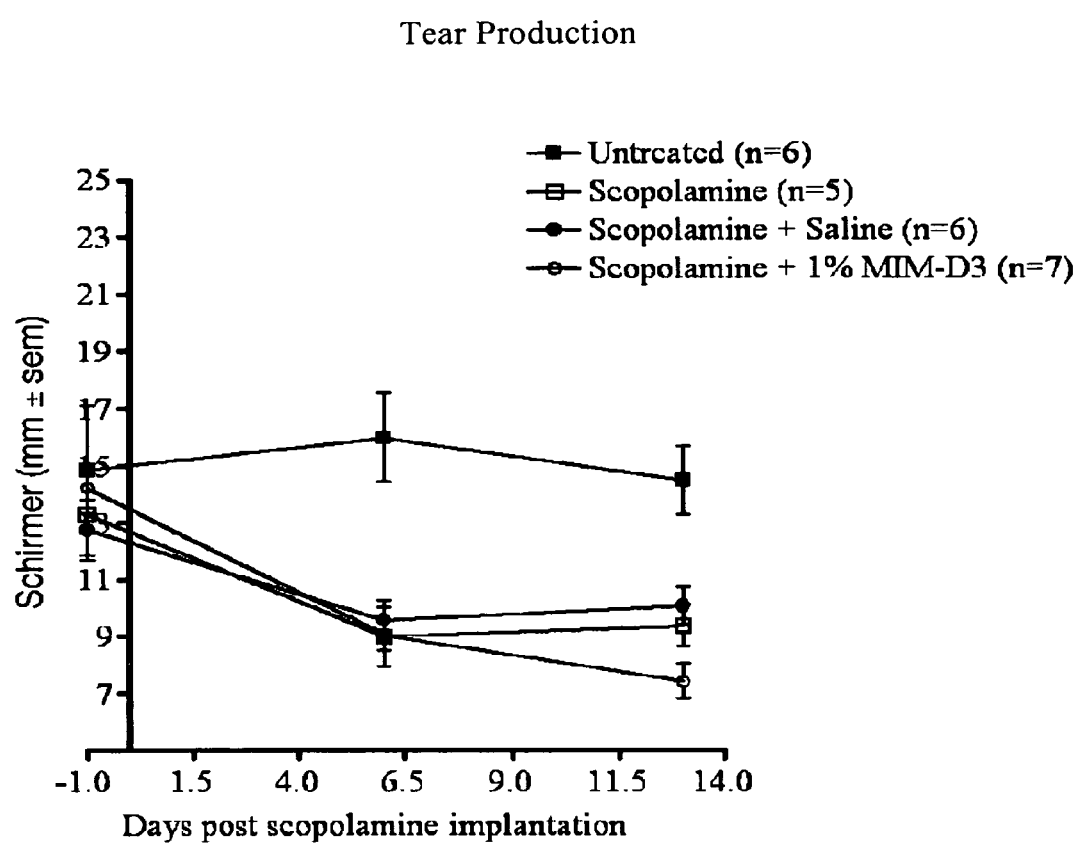
FIG. 12 is a graph of tear production scores (Schirmer test) (mm±sem) (Y axis) from negative control rats (untreated; n=6 rats), rats with dry eye model induced by systemic scopolamine continuously for fourteen days (scopolamine; n=5 rats), rats with dry eye model treated once topically on day eight with saline (scopolamine+saline; n=6 rats), and rats with dry eye model treated once topically on day eight with 50 ug of 1% compound D3 (scopolamine+1% compound D3; n=7 rats) in days post scopolamine implantation (X axis).

At baseline, the mean pre-treatment Schirmer score for all groups was 13.7±4.2 mm (P=0.6943). After six days, scopolamine treated animals had lower Schirmer scores (i.e. less tears) than untreated controls (9.2±2.5 mm compared to 16.0±5.4 mm, P<0.0001), corresponding to dry eye induction. A single topical dose with saline (Group 3) or 1% compound D3 (Group 4) on day eight, was followed by a 5-day no treatment period. On day thirteen, the groups receiving scopolamine had statistically significant lower Schirmer scores than untreated control (Group 1) (P<0.0001), with no statistically significant difference among dosed groups (FIG. 12). A single topical instillation of 1% compound D3 on day eight has no effect on aqueous tear production as measured at day thirteen (five days later) compared to the untreated or scopolamine treated controls.

Tear Fluorescein Clearance:

Tear fluorescein clearance was evaluated as described for humans (Afonso, A A. et al., "Correlation of Tear Fluorescein Clearance and Schirmer Test Scores with Ocular Irritation Symptoms," Ophthalmology 106:803-810 (1999), the entire content of which is incorporated herein by reference) and modified for rats (Chen, W. et al., "Keratoconjunctivitis Sicca Modifies Epithelial Stem Cell Proliferation Kinetics in Conjunctiva," Cornea 26:1101-1106 (2007), the entire content of which is incorporated herein by reference). Animals were lightly sedated with Isoflurane and two microliters of 1% sodium fluorescein (Sigma-Aldrich, St. Louis, Mo.) solution (in sterile saline) was applied to the lower conjunctival sac. The animals awoke within two minutes. After fifteen minutes, the animals were re-sedated and the fluorescein-stained tear fluid was collected with a phenol-red cotton thread (exactly as for Schirmer testing). The threads were immediately sealed in 1.5 mL polypropylene Eppendorf tubes shielded from light until fluorophotometric analysis. The length of cotton wetting in mm determined the volume of the collected tear fluid.

After, 100 µL of phosphate-buffered saline (PBS) was added, the tubes were spun at 12,000 rpm for five minutes and the fluid transferred to a 96-well polystyrene microtiter plate (Corning Life Sciences #2592, Fisher Scientific, Nepean, Ont.). A standard well was prepared on each plate, which consisted of a phenol-red thread placed in 100 µl PBS containing 2 µl of 1% sodium fluorescein solution. Fluorescence was measured immediately using a fluorescence microplate reader (FLUOstar OPTIMA, BMG Labtech, Germany) after setting the gain to the standard well. The concentration of fluorescein in tears was calculated from the fluorescence units (FU) divided by the mm of cotton wetting (FU/mm).

Figure 13:
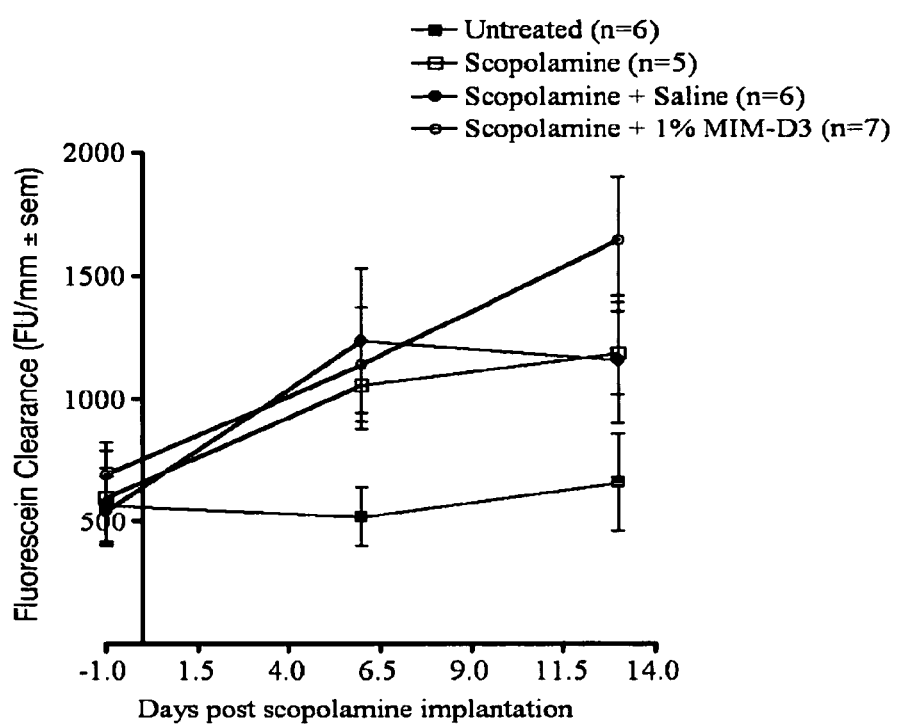
FIG. 13 is a graph of tear fluorescein clearance scores (FU/mm±sem) (Y axis) from negative control rats (untreated; n=6 rats), rats with dry eye model induced by systemic scopolamine continuously for fourteen days (scopolamine; n=5 rats), rats with dry eye model treated once topically on day eight with saline (scopolamine+saline; n=6 rats), and rats with dry eye model treated once topically on day eight with 50 ug of 1% compound D3 (scopolamine+1% compound D3; n=7 rats) in days post scopolamine implantation (X axis).

Aqueous tear turnover was measured by fluorescein clearance. At baseline, the mean fluorescein clearance value was 606±496 FU/mm (P=0.8920). At subsequent examinations on day six and thirteen, numerically, the groups receiving scopolamine had higher values (i.e., less tear turnover) than the Group 1 (untreated control). This difference was statistically significant at day 13 (0.0304), but not day 6 (P=0.1117) (FIG. 13). A single topical instillation of 1% compound D3 on day eight has no effect on aqueous tear turnover as measured at day thirteen (5 days later) compared to the untreated or scopolamine treated controls.

Statistical Analysis:

The mean and standard deviation (SD) were used to characterize the data for each study group. A one-way analysis of variance (ANOVA) was performed for body weight and the ophthalmic signs for treatment groups at every observation using GraphPad Prism 4.0c (GraphPad Software Inc., La Jolla, Calif.). When stratified by examination day, when the treatment group was statistically significant (p<0.05, two-tail), pair wise comparisons were performed. For comparison to the untreated control (Group 1 or A), adjustment with Dunnett's test was used. No corrections were made for multiple comparisons. The among group P values are not shown and the difference between each of a pair of means (reported P values as >0.05, <0.05, <0.01 or <0.001) are not shown.

Example 4

Tear Mucin Production in Naïve Rats Following Topical Instillation of Compound D3

Dose-ranging studies were conducted on the topical instillations of compound D3 in stimulating mucin production in naïve rats. Thirty male sprague dawley rats were divided into five groups of six rats per group and were treated bilaterally once every hour for six consecutive hours with either saline, 0.4% of compound D3, 1.0% of compound D3, 2.5% of compound D3 and 0.00053% of NGF. Once anesthetized, each animal received a 5 µL topical instillation of test article into the lower conjunctival sac of both eyes using a calibrated micropipette.

Tear fluid washings from both eyes were pooled and were collected prior to treatment and following six hourly instillations of saline, compound D3 and NGF. All tear fluid washings were evaluated for mucin concentration by an enzyme-linked lectin assay (ELLA).

The mean and standard deviation (SD) were used to characterize the data. The differences in mucin concentration was calculated from treated minus baseline from groups of rats. Continuous mucin changes between two groups from baseline were evaluated using the paired t test. The mucin changes between more than two treatment groups were analyzed using an analysis of variance. The median mucin changes between treatment groups were compared against a theoretical median of zero using the Wilcoxon rank sum test. A two-sided test with P<0.05 was considered to be statistically significant. Statistical analysis were performed using GraphPad Prism 4.0C (GraphPad Software Inc., La Jolla, Calif.).

Figure 14:
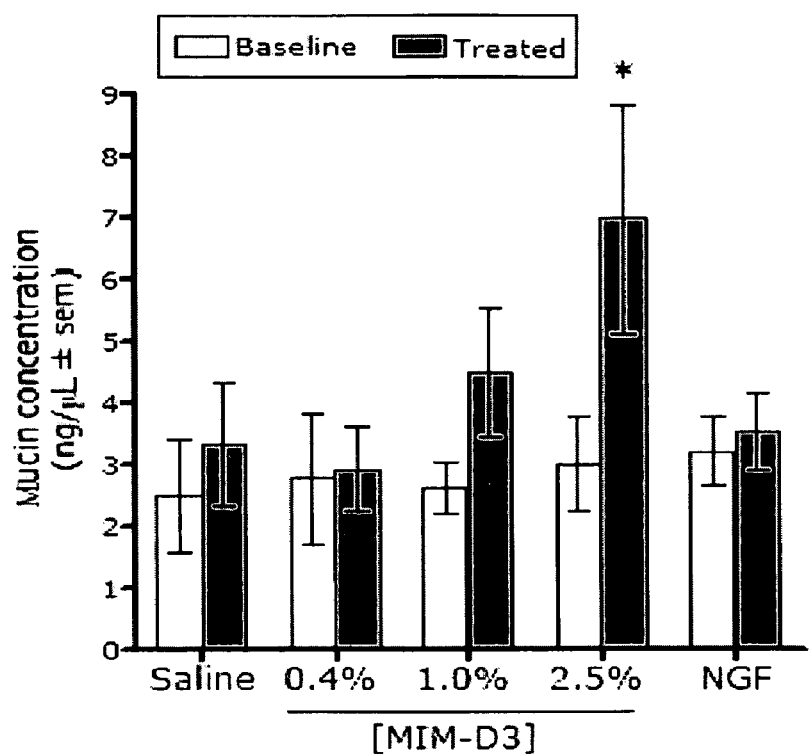
FIG. 14 is a bar graph showing the mucin concentration prior to and after topical administration of compound D3 and NGF treatment in normal rats. The Y axis represents mucin concentration (ng/µL±sem). The X axis represents saline and compound D3 (0.4, 1.0 and 2.5%) and NGF.
Figure 15:
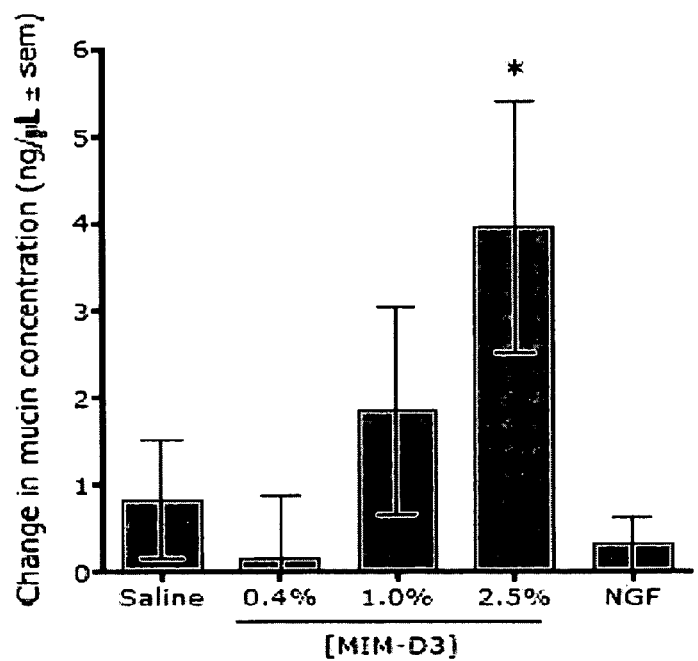
FIG. 15 is a bar graph showing the change in mucin concentration from baseline after topical administration of compound D3 and NGF treatment in normal rats. The Y axis represents change in mucin concentration (ng/µL±sem). The X axis represents saline and compound D3 (0.4, 1.0 and 2.5%) and NGF.

The results demonstrated that, after treatment, the difference among groups was not statistically significant (p=0.1430). When pair wise comparisons were made between treated to baseline, there was a statistically significant increase in mucin concentration in animals treated with 2.5% compound D3 (FIG. 14) (from 3.0±1.9 ng/µL to 7.0±4.5 ng/µL, p=0.0413), but not other groups (p=0.1799 to 8454). In addition, the difference among groups was not statistically significant (p=0.0818). When the difference among groups were compared against a theoretical median of zero, there was a statistically significant increase in the group treated with 2.5% of compound D3 (4.0±3.5 ng/µL p-0.0312), but not other groups (p=0.1562 to 1.1250). Numerically, the increases in mean changes in mucin concentration in all of the groups treated with compound D3 were dose-dependent (FIG. 15).

Example 5

Scopolamine Induced Rat Dry Eye Model
(Compound D3 and Nerve Growth Factor)

Animals:

Male Sprague-Dawley rats (six to eight weeks old) weighing between 360 g and 470 g were obtained from Charles River (Wilmington, Mass.). Animals were housed in animal quarters under constant room temperature (22±1° C.), light conditions (12-h light/12-h dark cycle), and relative humidity (32-61%). Animals were anaesthetized before the surgical pump implantation and before all clinical endpoint testing in an isoflurane 99.9% (Abraxis Bioscience, Richmond Hill, Ontario) chamber.

Induction of Dry Eye by Cholinergic Blockade:

Dry eye was induced using scopolamine hydrobromide (Sigma-Aldrich, St. Louis, Mo.), which was continuously and systemically delivered to the animals via an osmotic pump (2ML4 Alzet®; CedarLane, Burlington, Ontario) filled with scopolamine and implanted subcutaneously in the mid dorsal area between the scapulae. Scopolamine was delivered for a twenty-eight day period at 12.5 mg/day, which translated to 30.0±1.5 mg/kg via osmotic pump.

A sterile solution of 0.175 g/mL of scopolamine hydrobromide (Sigma-Aldrich, St. Louis, Mo.) was prepared in saline. The solution was filtered through a 0.22 um syringe-end filter (Millex-GC, Millipore Corp, Bedford, Mass.), and stored refrigerated overnight. Alzet® Osmotic pumps (Model 2ML4, LOT NO. 10187-08, CedarLane Laboratories, Burlington, Ontario) were filled with 2 mL of the scopolamine solution according to the manufacturer's instructions. Sterile technique was used during the filling and handling of the pumps.

After the surgery and again the next day, the animals were subcutaneously injected with Caprofen (0.5 mg/100 g) a non-steroidal anti-inflammatory drug and potent, long-acting analgesic in rodents. Animals were weighed prior to pump implantation on Day-1, and then once a week for four weeks. This dosing regimen was reported to induce dry eye in rats (Viau S et al., "Time course of ocular surface and lacrimal gland changes in a new scopolamine-induced dry eye model," *Graefes Arch Clin Exp Ophthalmol.*, 246:857-867 (2008), the entire content of which is incorporated herein by reference).

Treatment Groups:

As seen in Table 3 and FIG. 16, the groups of rat eyes tested were as follows:

Control rats (n=10 eyes from 5 rats) without pumps implanted and were not treated throughout the study (this group is also referred to herein as "G1").

Rats (n=10 eyes from 5 rats) were induced with dry eye by systemic administration of scopolamine continuously and treated daily topically with 5 µL saline starting on day five and continuing through day twenty-one (this group is also referred to herein as "G2").

Rats (n=10 eyes from 5 rats) were induced with dry eye by systemic administration of scopolamine continuously and treated daily topically with 5 µL of a 0.4% (4 mg/mL) solution of compound D3 starting on day five and continuing through day twenty-one (this group is also referred to herein as "G3").

Rats (n=10 eyes from 5 rats) were induced with dry eye by systemic administration of scopolamine continuously and treated daily topically with 5 µL of a 1.0% (10 mg/mL) solution of compound D3 starting on day five and continuing through day twenty-one (this group is also referred to herein as "G4").

Rats (n=10 eyes from 5 rats) were induced with dry eye by systemic administration of scopolamine continuously and treated daily topically with 5 µL of a 2.5% (25 mg/mL) solution of compound D3 starting on day five and continuing through day twenty-one (this group is also referred to herein as "G5").

Rats (n=10 eyes from 5 rats) were induced with dry eye by systemic administration of scopolamine continuously and treated daily topically with 5 µL of a 0.00053% (0.00526 mg/mL) solution of NGF starting on day five and continuing through day twenty-one (this group is also referred to herein as "G6").

Treatments for G2-G6 continued daily for seventeen days (up to an including day twenty-one). Thereafter, treatments were terminated but the study continued for another week. During treatment, each animal was anesthetized in an isoflurane chamber. Once asleep, each animal received a 5 µL topical instillation of test article into the lower conjunctival sac of both eyes using a calibrated micropipette. If a clinical endpoint was also being tested, the test article was topically instilled at the end of the testing.

TABLE 3

| | | | Treatment Groups | | | | |
|---|---|---|---|---|---|---|---|
| Group | Scopolamine | No. Rats | Test Article (Both Eyes) | Route (bilateral) | Frequency | Dose Volume | Test Article Concentration (%) |
| G1 | No | 5 | — | — | — | — | — |
| G2 | Yes | 5 | Saline | Topical instillation | 1x daily, Days 5-21 | 5 µL | — |
| G3 | Yes | 5 | Compound-D3 | Topical instillation | 1x daily, Days 5-21 | 5 µL | 0.4 |
| G4 | Yes | 5 | Compound-D3 | Topical instillation | 1x daily, Days 5-21 | 5 µL | 1.0 |

TABLE 3-continued

Treatment Groups

| Group | Scopolamine | No. Rats | Test Article (Both Eyes) | Route (bilateral) | Frequency | Dose Volume | Test Article Concentration (%) |
|---|---|---|---|---|---|---|---|
| G5 | Yes | 5 | Compound-D3 | Topical instillation | 1x daily, Days 5-21 | 5 µL | 2.5 |
| G6 | Yes | 5 | NGF | Topical instillation | 1x daily, Days 5-21 | 5 µL | 0.00053 |

Dosing Solution Preparation

Compound D3 was prepared using a formulation designed by Mimetogen Pharmaceuticals, which is buffered saline ~pH 7 (as determined by pH indicator strips, EMD Chemicals). Three topical dosing solutions were prepared as follows:

A topical dosing solution of 0.4% was prepared using 4.0 mg of compound dissolved in 845 µL of sterile milliQ water. The solution was adjusted to ~pH 7 with 6.5 µL of 1.0 N NaOH (VWR) using pH indicator strips and made isotonic (0.9% NaCl) by adding 148.5 µL of sterile 1.0 M NaCl.

A topical dosing solution of 1.0% was prepared using 10.0 mg of compound dissolved in 845 µL of sterile milliQ water. The solution was adjusted to ~pH 7 with 20 µL of 1.0 N NaOH, and made isotonic by adding 135 µL of sterile 1.0 M NaCl.

A solution of 2.5% (maximum solubility) was prepared using 25.0 mg of compound dissolved in 845 µL of sterile milliQ water. The solution was adjusted to ~pH 7 with 20 µL of 1.0 N NaOH. The solution was made isotonic by adding 135 µL of sterile 1.0 M NaCl. All solutions were sonicated for 5 min. All compound D3 solutions were stored refrigerated (2-8° C.) for the duration of the study.

One topical dosing solution of 0.00053% NGF was prepared by diluting 1 µL of the 3.16 mg/mL stock solution in 600 µL of sterile 0.9% sodium chloride injection, USP (LOT 63-922-FW EXP 20100301). A freshly diluted dosing solution was made every week, and stored refrigerated (2-8° C.). This concentration of NGF was reported to have efficacy in i) dogs that developed dry eye after the excision of the third eyelid lacrimal gland (Coassin M, Lambiase A, Costa N, et al: Efficacy of topical nerve growth factor treatment in dogs affected by dry eye. Graefe's Archive for Clinical and Experimental Ophthalmology 2005; 243:151-155, which is incorporated herein by reference in its entirety) and ii) rabbits that develop corneal nerve damage after Photorefractive keratectomy (PRK) (Esquenazi S, Bazan HEP, Bui V, et al: Topical Combination of NGF and DHA Increases Rabbit Corneal Nerve Regeneration after Photorefractive Keratectomy. Investigative Ophthalmology & Visual Science 2005; 46:3121-3127, the entire content of which is incorporated herein by reference).

A topical dosing solution of sterile 0.9% sodium chloride injection, USP (LOT 63-922-FW EXP 20100301) was used. The saline solution was stored at room temperature.

Clinical Endpoints for Dry Eye and Results:

As discussed in detail below, evaluation of the effects of the 0.4, 1.0 or 2.5% doses of compound D3 following the seven day recovery period, showed that the 1% dose of compound D3 increased tear break-up time (TBUT), increased mucin production and almost completely restored corneal staining, as compared to the untreated control, but did not show any statistically significant difference as compared to control for tear production (Schirmer test), protein determination or fluorescein clearance.

TBUT:

Tear break-up times were tested on day 13 (after 8 daily treatments), day 21 (after 16 daily treatments), and day 28 (after treatment was stopped for 7 days). TBUT was evaluated by instillation of 10 µL sodium fluorescein solution (0.2% in sterile saline) in the upper conjunctival sac of the anaesthetized animal. The lids were blinked manually to distribute the fluorescein with the tear film. Under the cobalt blue light of a portable slit lamp ophthalmoscope (Reichert Ophthalmic Instruments, Depew, N.Y.), the eye was held open and the time until one or more black streaks appeared in the precorneal tear film was recorded. For each eye, a minimum of triplicate readings were made with fresh fluorescein solution.

Figure 17A:
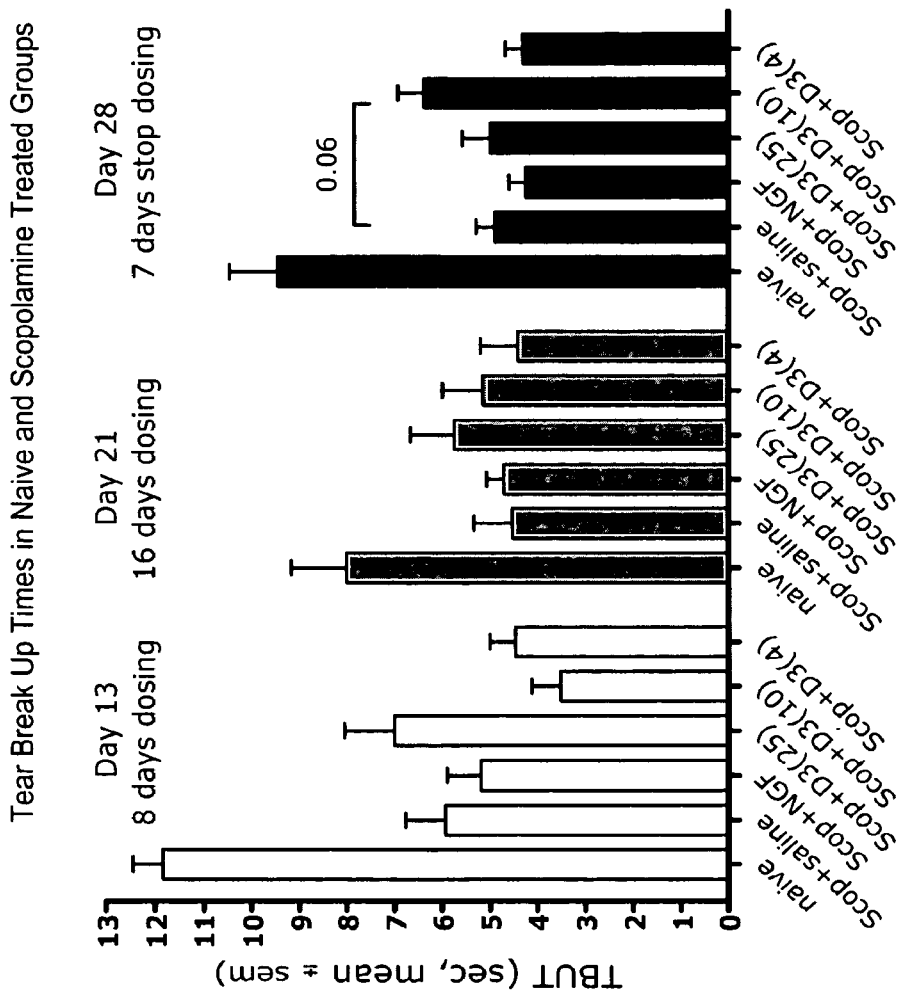
FIG. 17A is a bar graph of tear break-up time (TBUT) (sec, mean±sem) in naïve and scopolamine implanted rats treated with saline, 0.00053% NGF and compound D3 at 2.5%, 1.0% and 0.4% (which correspond to compound D3 at 25 mg/mL, 10 mg/mL and 4 mg/mL, respectively) at day 13, day 21 and day 28. The Y axis represents TBUT (sec, mean±sem). The X axis represents naïve and scopolamine implanted rats treated with saline, 0.00053% NGF and compound D3 at 2.5%, 1.0% and 0.4% at day 13, day 21 and day 28.
Figure 17B:
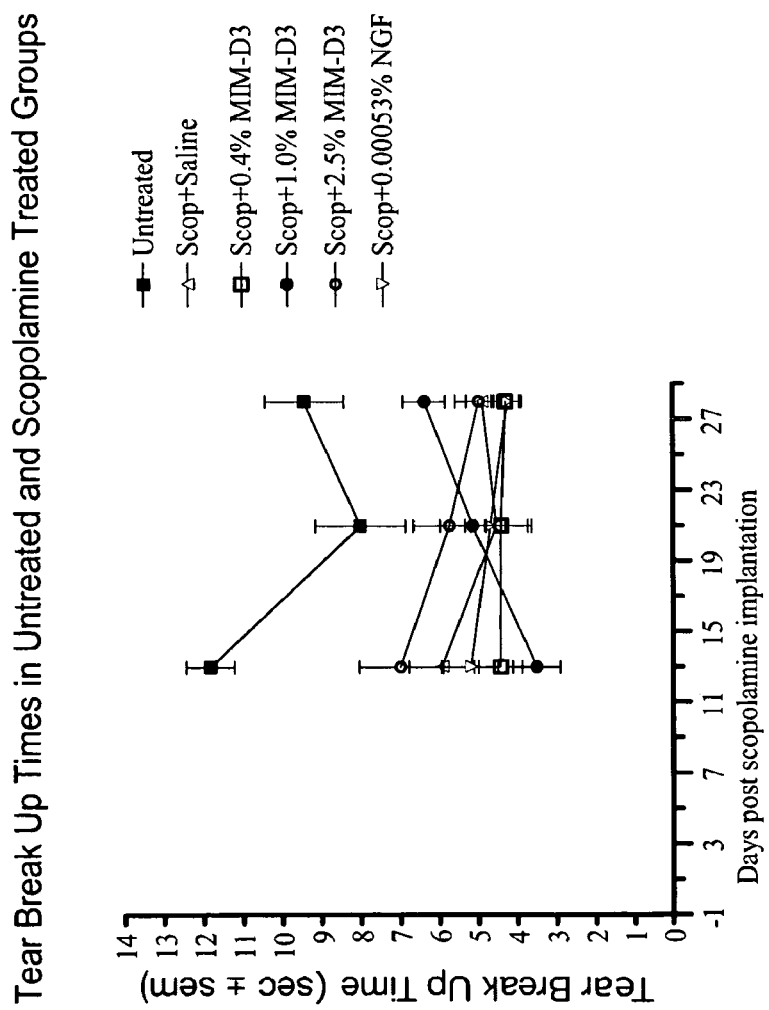
FIG. 17B is a plot of tear break-up time (TBUT) (sec±sem) (Y axis) in naïve and scopolamine implanted rats treated with saline, compound D3 at 0.4%, 1.0%, 2.5%, and 0.00053% NGF in days post scopolamine implantation (X axis).

Tear break up time was highest (i.e., better) in Group 1 (untreated control) than in any of the groups receiving scopolamine (Table 4 and FIGS. 17A and B). There was a statistically significant effect of treatment at all observations ($p<0.0001$, 0.0349, and $<0.0001$, respectively). During treatment (Day 13), all groups receiving scopolamine were statistically significantly different from Group 1 ($p<0.0001$ to 0.0012). When further pair wise comparisons were made for Group 5 (7.0±2.3 sec, 2.5% Compound D3), statistically significant differences were seen from the Group 4 (3.9±1.2 sec, 1.0% Compound D3, $p=0.0160$). During treatment (Day 21), all groups receiving scopolamine were statistically significantly different from Group 1 ($p=0.0167$ to 0.0289), with the exception of Groups 4 and 5 (1.0% and 2.5% Compound D3). On Day 28, all groups receiving scopolamine were statistically significantly different from Group 1 ($p<0.0001$ to 0.0054). When further pair wise comparisons were made for Group 4 (6.4±1.2 sec, 1.0% Compound D3), statistically significant differences were seen from the Group 3 (4.3±0.8 sec, 0.4% Compound D3, $p=0.0204$) and the Group 6 (4.2±0.8 sec, NGF, $p=0.0165$). After the seven day recovery period, the 1% dose of compound D3 increased TBUT as compared to the untreated control. In contrast, there was no difference in TBUT for the 0.4% and 2.5% doses of compound D3 following the seven day recovery period. The higher dose may have desensitized the NGF receptors on the goblet cells causing them to be refractory to the agonist activity of compound D3. The lower dose may have been just sub-optimal.

Figure 20A:
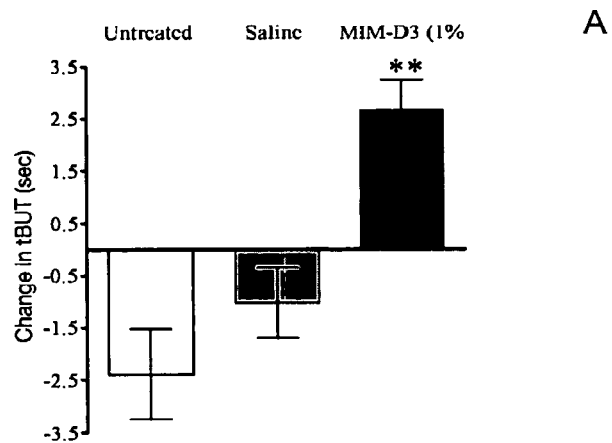
FIGS. 20A-C show bar graphs the effect of compound D3 on selected endpoint measurements.
Figures 21A, 21B, 21C:
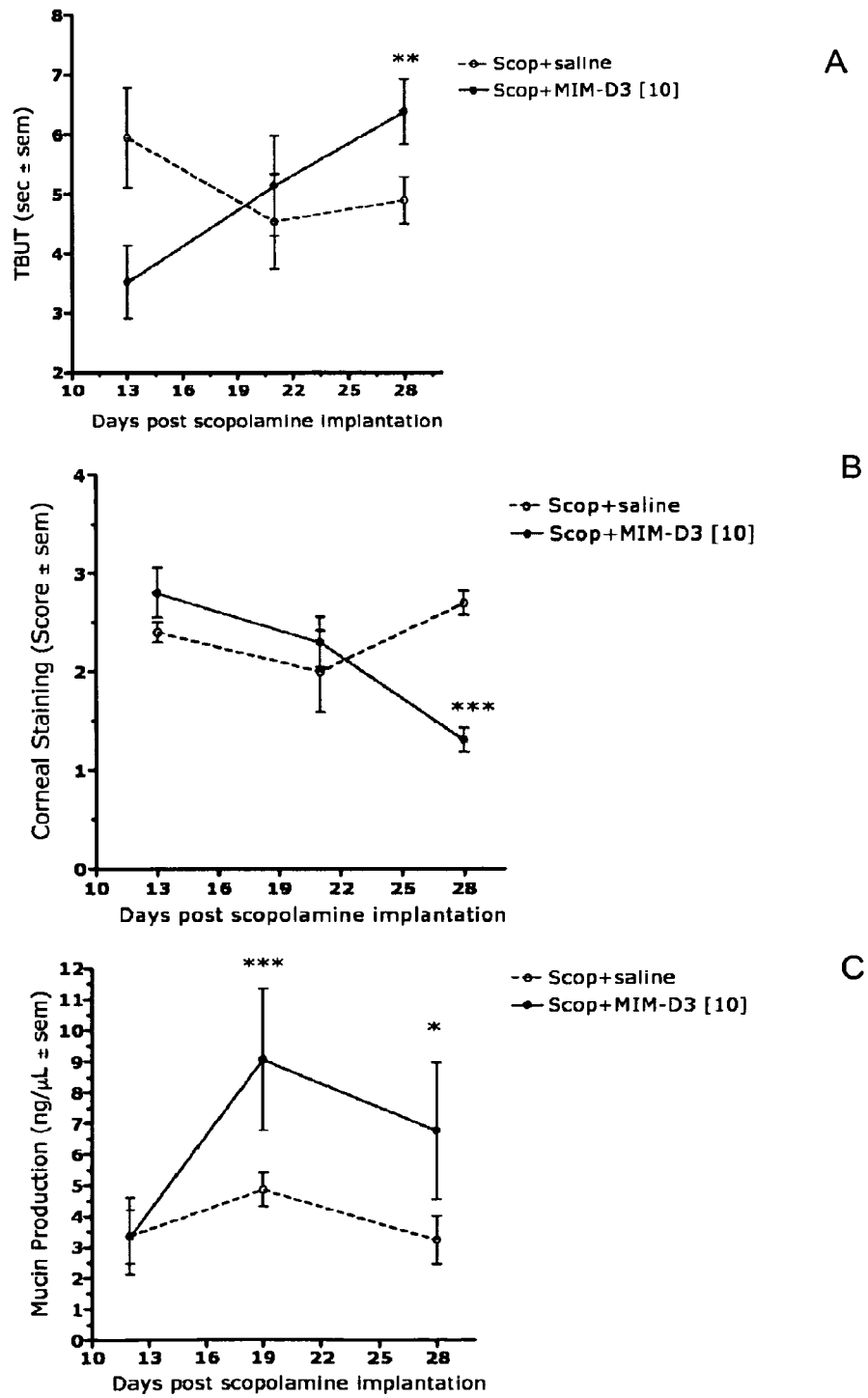
FIGS. 21A-C show plots of the effect of 1% compound D3 on selected endpoint measurements.

While there are no baseline values for TBUT, the effect of the 1% dose of compound D3 compared to the untreated control group and saline group can be appreciated by evaluating the changes in TBUT at Day 28 as compared to Day 13. The 1% dose of compound D3 statistically significantly improved TBUT as compared to the untreated and saline control groups ($p=0.0001$) (FIG. 20A). In addition, FIG. 21A illustrates endpoint measurement data for TBUT over time as compared to Day 13 in the saline control group and the group treated with 1% dose of compound D3.

TABLE 4

Tear Break-Up Time Data

Tear Break-Up Time (seconds ± SD)

| | Groups[5a] | | | | | | |
|---|---|---|---|---|---|---|---|
| Day | 1 | 2 | 3 | 4 | 5 | 6 | P value |
| 13 | 11.8 ± 1.4 | 5.9 ± 1.9 | 4.5 ± 1.7[b] | 3.9 ± 1.2[c] | 7.0 ± 2.3 | 5.2 ± 1.6 | <0.0001 |
| 21 | 8.0 ± 2.6 | 4.5 ± 1.8 | 4.4 ± 1.7 | 5.1 ± 1.9 | 5.8 ± 2.1 | 4.7 ± 0.8 | 0.0523 |
| 28 | 9.4 ± 2.3 | 4.9 ± 0.9 | 4.3 ± 0.8 | 6.4 ± 1.2 | 5.0 ± 1.3 | 4.2 ± 0.8 | <0.0001 |

[a]n = 5 at every observation, except at Day 13 for G3 and G4
[b]n = 3
[c]n = 4
[5]Group Code:
1) Naive;
2) Scopolamine + Saline;
3) Scopolamine + 0.4% Compound D3;
4) Scopolamine + 1.0% Compound D3;
5) Scopolamine + 2.5% Compound D3;
6) Scopolamine + 0.00053% NGF Corneal Staining:

Immediately following TBUT assessment, the clinical signs of corneal dryness were evaluated by fluorescein staining of the cornea and was tested on day 13 (after 8 daily treatments), day 21 (after 16 daily treatments), and day 28 (after treatment was stopped for 7 days). A drop of a 0.2% sodium fluorescein solution made up in sterile saline was instilled in the upper conjunctival sac of the anaesthetized animal. The cornea was thereafter observed under blue light using a Portable Slit Lamp ophthalmoscope with blue cobalt filter (Reichert Ophthalmic Instruments, Depew, N.Y.) two to three minutes after fluorescein instillation. For each animal, the punctate fluorescein-stained area of the cornea was recorded in a masked fashion. The score of this test was graded from 0 to 4, where 0 is equal to no staining, 1 is less than 25% surface staining, 2 is 25-50% surface staining, 3 is 50-75% surface staining, and 4 is greater than 75% surface staining.

Figure 18A:
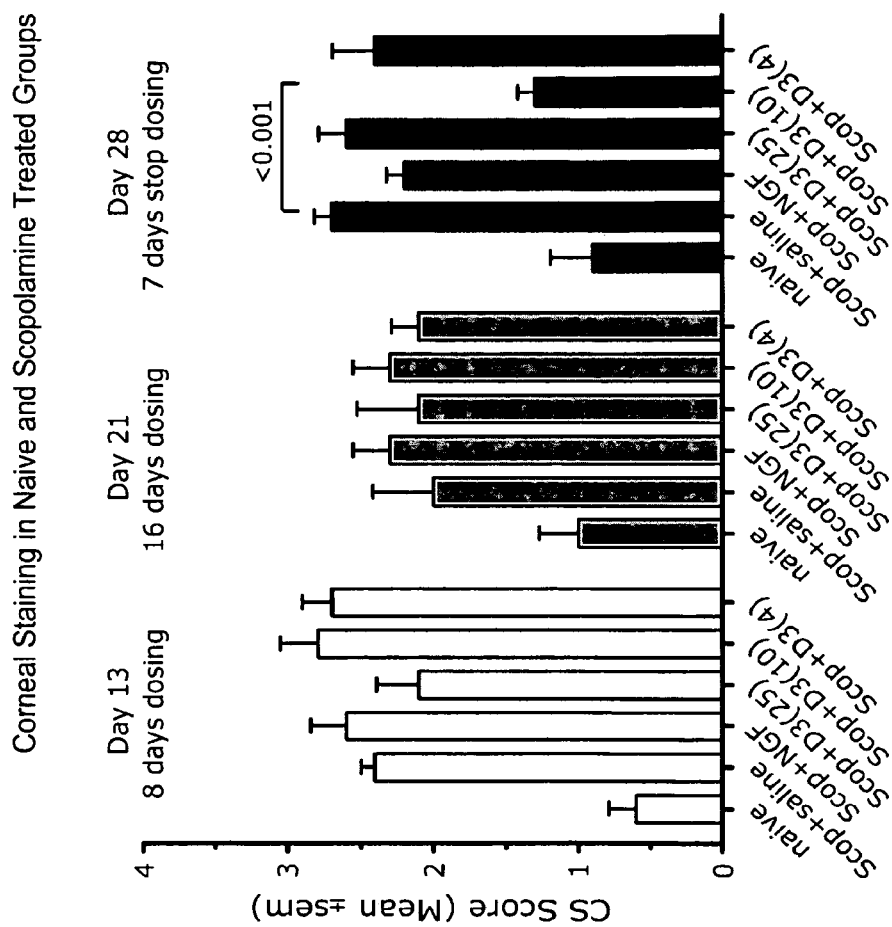
FIG. 18A is a bar graph of corneal staining (mean±sem) in naïve and scopolamine implanted rats treated with saline, 0.00053% NGF and compound D3 at 2.5%, 1.0% and 0.4% (which correspond to compound D3 at 25 mg/mL, 10 mg/mL and 4 mg/mL, respectively) at day 13, day 21 and day 28. The Y axis represents corneal staining (CS) (sec, mean±sem). The X axis represents naïve and scopolamine implanted rats treated with saline, 0.00053% NGF and compound D3 at 2.5%, 1.0% and 0.4% at day 13, day 21 and day 28.
Figure 18B:
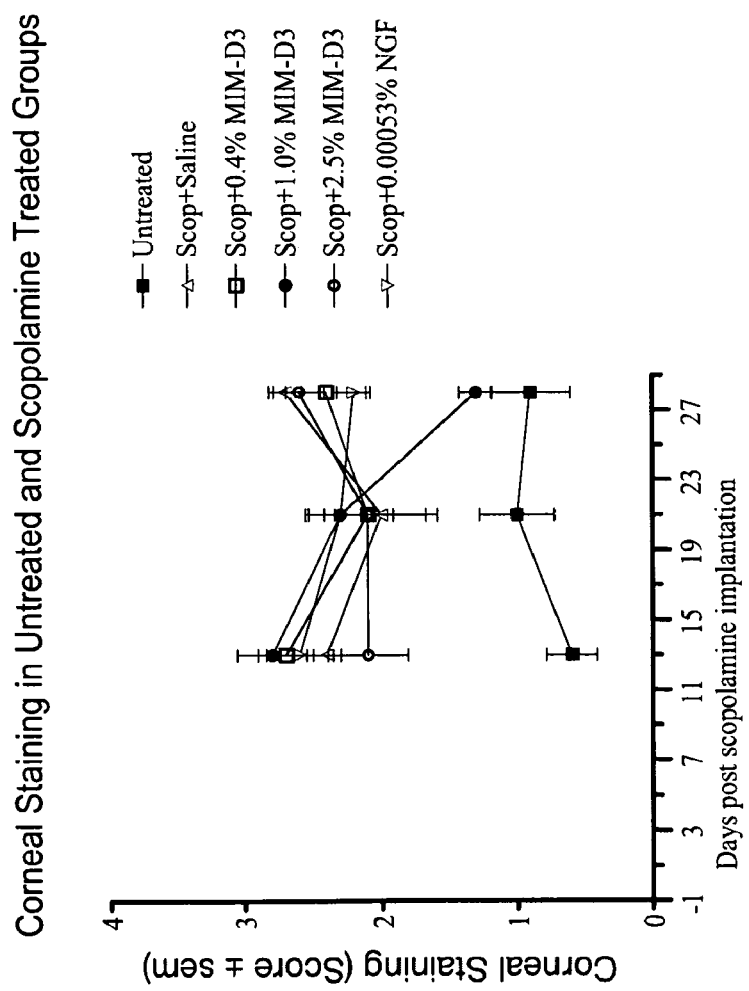
FIG. 18B is a plot of corneal staining (score±sem) (Y axis) in naïve and scopolamine implanted rats treated with saline, compound D3 at 0.4%, 1.0%, 2.5%, and 0.00053% NGF in days post scopolamine implantation (X axis).

Numerically, the groups receiving scopolamine had higher values (i.e., more damage) than the Group 1 (untreated control) (Table 5 and FIGS. 18A-B). The difference among groups was statistically significant at Days 13 and 28 ($p<0.0001$), but not Day 21 ($p=0.0682$). On Day 13, each of the groups receiving scopolamine was statistically significantly different from Group 1 ($p<0.0001$ to $0.0003$), but not from each other ($p>0.0677$), with the exception of Group 5, which was statistically significantly different from the Group 4 ($p=0.0352$). On Day 28, Groups 2, 3, 5 and 6 were statistically significantly different from Group 1 ($p<0.0001$ to $0.0007$). The mean value in Group 4 (1% Compound D3), 1.3±0.3, was not statistically significantly different from the Group 1 (untreated control, 0.9±0.7, $p=0.5136$). As well, at this examination, Group 4 was statistically significantly different from the higher values seen in Groups 2, 3, 5 and 6 ($p<0.0001$ to $0.0047$). After the seven day recovery period, the 1% dose of compound D3 almost completely restored corneal staining as compared to the untreated control group. In contrast, there was no difference in corneal staining for the 0.4% and 2.5% doses of compound D3 doses following the seven day recovery period. The higher dose may have desensitized the NGF receptors on the goblet cells causing them to be refractory to the agonist activity of compound D3. The lower dose may have been just sub-optimal.

Figure 20B:
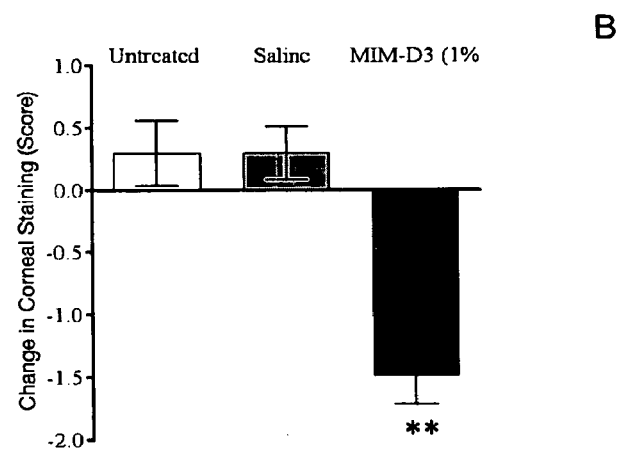

While there are no baseline values for corneal staining, the effect of the 1% dose of compound D3 compared to the untreated control group and saline group can be appreciated by evaluating the changes in corneal staining at Day 28 as compared to Day 13. The 1% dose of compound D3 dose statistically significantly improved corneal staining as compared to the untreated and saline control groups ($p<0.0001$) (FIG. 20B). In addition, FIG. 21B illustrates endpoint measurement data for corneal staining over time as compared to Day 13 in the saline control group and the group treated with 1% dose of compound D3.

TABLE 5

Corneal Staining Data

Corneal Staining (Score ± SD)[a]

| | Groups[6b] | | | | | | |
|---|---|---|---|---|---|---|---|
| Day | 1 | 2 | 3 | 4 | 5 | 6 | P value |
| 13 | 0.6 ± 0.4 | 2.4 ± 0.2 | 2.7 ± 0.4 | 2.8 ± 0.6 | 2.1 ± 0.7 | 2.6 ± 0.5 | <0.0001 |
| 21 | 1.0 ± 0.6 | 2.0 ± 0.9 | 2.1 ± 0.4 | 2.3 ± 0.6 | 2.1 ± 1.0 | 2.3 ± 0.6 | 0.0682 |
| 28 | 0.9 ± 0.7 | 2.7 ± 0.3 | 2.4 ± 0.7 | 1.3 ± 0.3 | 2.6 ± 0.4 | 2.2 ± 0.3 | <0.0001 |

[a]Score: 0 to 4
[b]n = 5 at every observation
[6]Group Code:
1) Naive;
2) Scopolamine + Saline;
3) Scopolamine + 0.4% Compound D3;
4) Scopolamine + 1.0% Compound D3;
5) Scopolamine + 2.5% Compound D3;
6) Scopolamine + 0.00053% NGF A significant inverse correlation was noted between tBUT values and corneal staining scores between groups at all examinations. tBUT values decreased as corneal staining scores increased (Spearman r=−0.7606, p<0.0001, n=87 XY pairs).

Determination of Mucin Production:

Tear fluid washings were collected from all six groups of rats on day 12 (after 7 daily treatments), day 19 (after 14 daily treatments) and day 28 (after treatment was stopped for 7 days) after instillation of 5 µL sterile saline in the lower conjunctival sac of the anaesthetized animal. The lids were blinked gently to mix the tear film with the saline. The diluted tear fluid was collected with a 5 µL volume glass capillary tube (Drummond Scientific Co, Broomhall, Pa.) by capillary action from the tear meniscus in the lateral canthus. Approximately 4-5 µL were routinely collected. In very dry eyes, a second 5 µL aliquot of saline was instilled before collection.

The concentrations of mucin glycoprotein in the diluted tear fluid washings were determined by an enzyme-linked lectin assay (ELLA). A sample containing 3 µg total protein was diluted to 100 µL in carbonate buffer pH 9.2 and transferred to a 96-well polystyrene microtiter plate (Corning Life Sciences #2592, Fisher Scientific, Nepean, Ontario). A dilution series of bovine submaxillary mucin (Sigma, St. Louis, Mo.) was included on each plate as the standard. The plates were coated by evaporation at 37° C. overnight. After, the plates were washed three times with wash buffer [PBS containing 0.3% BSA, 0.05% Tween-20] then blocked for non-specific binding with PBS containing 3% BSA and 0.05% Tween-20 at 37° C. for one hour. The wells were rinsed three times in wash buffer, and then incubated in 2 µg/mL biotinylated UEA-1 diluted in wash buffer (Vector Labs, Burlingame, Calif.) at 37° C. for one hour. The wells were rinsed three times in wash buffer, and then incubated in 1 µg/mL HRP-conjugated neutravidin diluted in wash buffer (Pierce, Rockford, Ill.) at 37° C. for one hour. After the wells were rinsed three times in wash buffer the color development was performed with TMB (Promega, Madison, Wis.) and stopped with 0.5N Sulfuric acid. The concentration of mucin in the tear fluid washings was calculated as the ng mucin divided by the volume of tear fluid washing in µL it that gave 3 µg total protein.

Figure 19A:
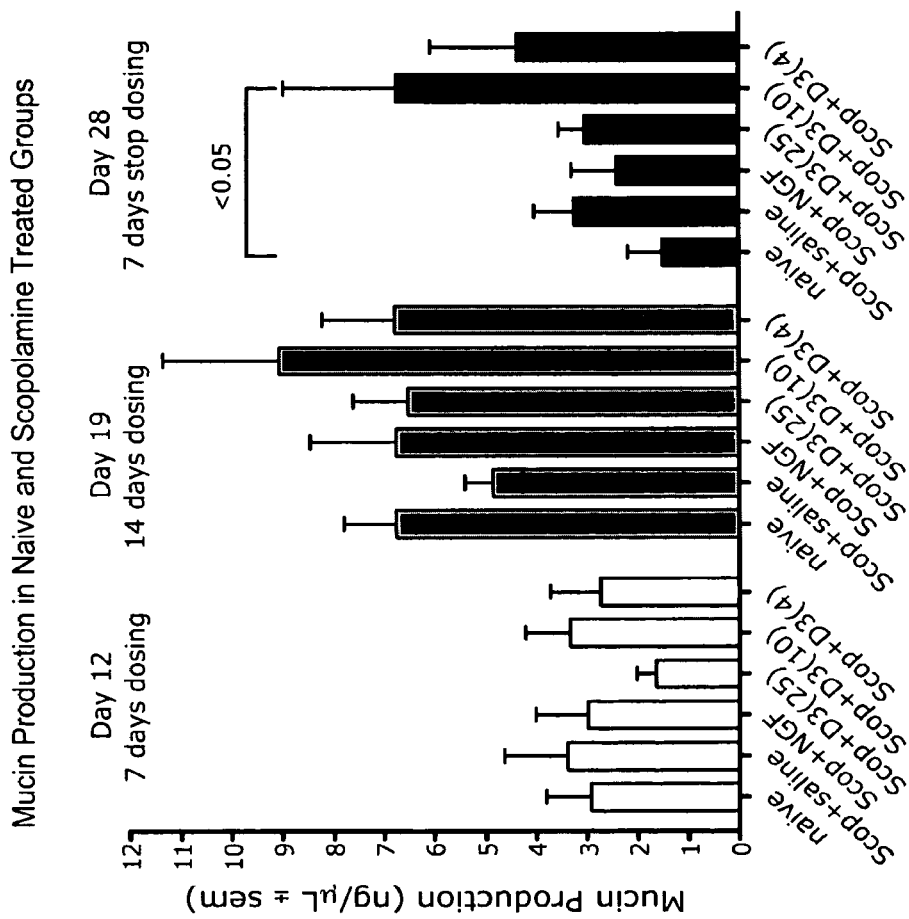
FIG. 19A is a bar graph of mucin production (ng/µL±sem) in naïve and scopolamine implanted rats treated with saline, 0.00053% NGF and compound D3 at 2.5%, 1.0% and 0.4% (which correspond to compound D3 at 25 mg/mL, 10 mg/mL and 4 mg/mL, respectively) at day 12, day 19 and day 28. The Y axis represents mucin production (ng/µL±sem). The X axis represents naïve and scopolamine implanted rats treated with saline, 0.00053% NGF and compound D3 at 2.5%, 1.0% and 0.4% at day 13, day 21 and day 28.
Figure 19B:
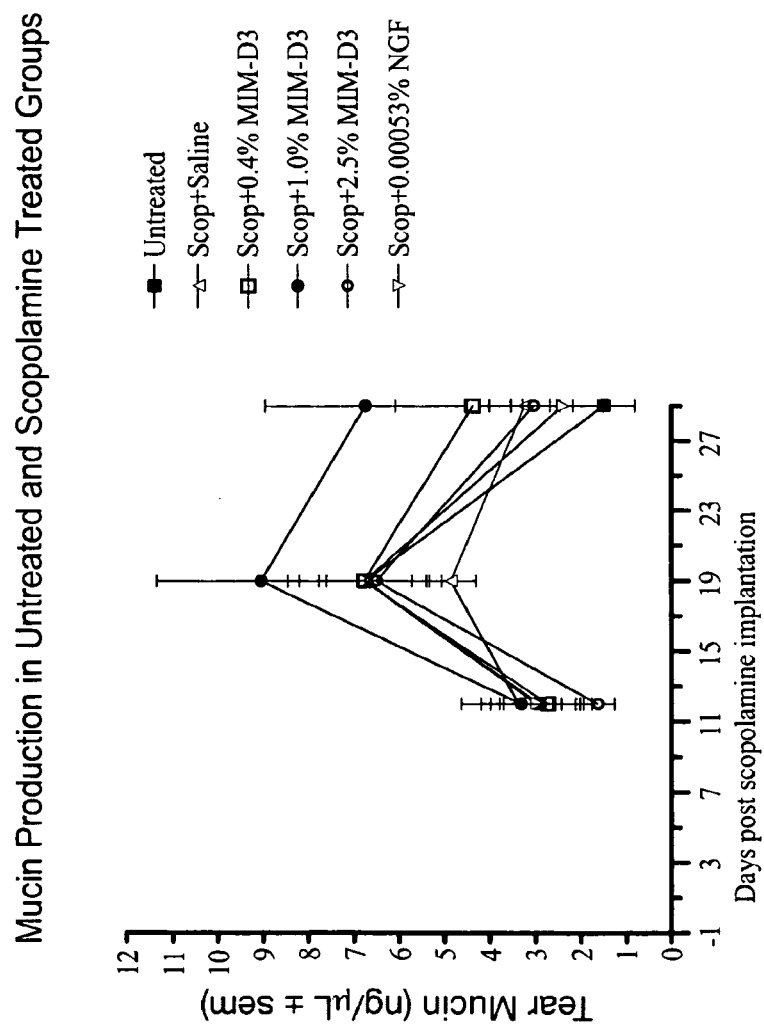
FIG. 19B is a plot of mucin production (ng/µL±sem) (Y axis) in naïve and scopolamine implanted rats treated with saline, compound D3 at 0.4%, 1.0%, 2.5%, and 0.00053% NGF in days post scopolamine implantation (X axis).

Mucin production was measured and the difference among groups was not statistically significant (p=0.1066 to 0.7844) at every observation (Table 6 and FIGS. 19A-B). Numerically, the highest mean values in any treatment group were seen in Group 4 (1% dose of compound D3) at each of these visits (3.3, 9.1 and 6.8 ng/µL), compared with Group 1 (untreated controls, 2.9, 6.8, and 1.5 ng/µL, respectively). This difference was statistically significant at day 28 (p=0.0312), but not other days (p=0.6992 to 0.9973). After the seven day recovery period, this statistically significant increase in mucin production by the 1% dose of compound D3 may have improved the quality and stability of the tear film. In contrast, there was no difference in mucin production for the 0.4% and 2.5% doses of compound D3 doses following the seven day recovery period. The higher dose may have desensitized the NGF receptors on the goblet cells causing them to be refractory to the agonist activity of compound D3. The lower dose may have been just sub-optimal.

Figure 20C:
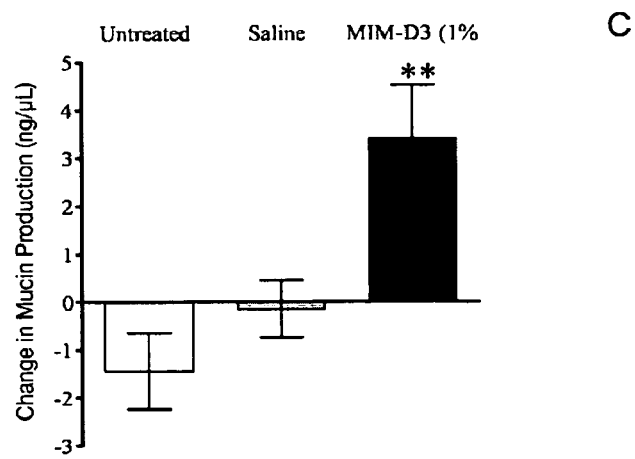

While there are no baseline values for mucin production, the effect of the 1% dose of compound D3 compared to the untreated control group and saline group can be appreciated by evaluating the changes in mucin production at Day 28 as compared to Day 12. The 1% dose of compound D3 statistically significantly increased mucin production as compared to the untreated and saline control groups (p=0.0013) (FIG. 20C). In addition, FIG. 21C illustrates endpoint measurement data for mucin production over time as compared to Day 12 in the saline control group and the group treated with 1% dose of compound D3.

TABLE 6

Mucin Production in Tear Fluid Washings

Tear Mucin (ng/µL ± SD)

| | Groups[7a] | | | | | | |
|---|---|---|---|---|---|---|---|
| Day | 1 | 2 | 3 | 4 | 5 | 6 | P value |
| 12 | 2.9 ± 2.0 | 3.4 ± 2.8 | 2.7 ± 2.2 | 3.3 ± 1.9 | 1.6 ± 0.9 | 3.0 ± 2.3 | 0.7844 |
| 19 | 6.8 ± 2.3 | 4.9 ± 1.2 | 6.8 ± 3.2 | 9.1 ± 5.1 | 6.5 ± 2.4 | 6.8 ± 3.8 | 0.5320 |
| 28 | 1.5 ± 1.5 | 3.2 ± 1.7 | 4.4 ± 3.8 | 6.8 ± 4.9 | 3.0 ± 1.1 | 2.4 ± 2.0 | 0.1066 |

[a] n = 5 at every observation
[7] Group Code:
1) Naive;
2) Scopolamine + Saline;
3) Scopolamine + 0.4% Compound D3;
4) Scopolamine + 1.0% Compound D3;
5) Scopolamine + 2.5% Compound D3;
6) Scopolamine + 0.00053% NGF Schrimer Test:

Tear production was monitored using the Schirmer test on days 5, 7, 14, 20 and 29 post induction of dry eye. Tear production was measured with Zone-Quick standardized phenol-red threads (FCI Ophthalmics, Marshfield Hills, Mass.) on animals lightly sedated with Isoflurane. The threads were inserted in the lateral lower canthus and left in place for thirty seconds. The length of the stained moistened portion of the thread was measured in millimeters, using the scale provided with the threads to an accuracy of 1 mm.

Figure 22:
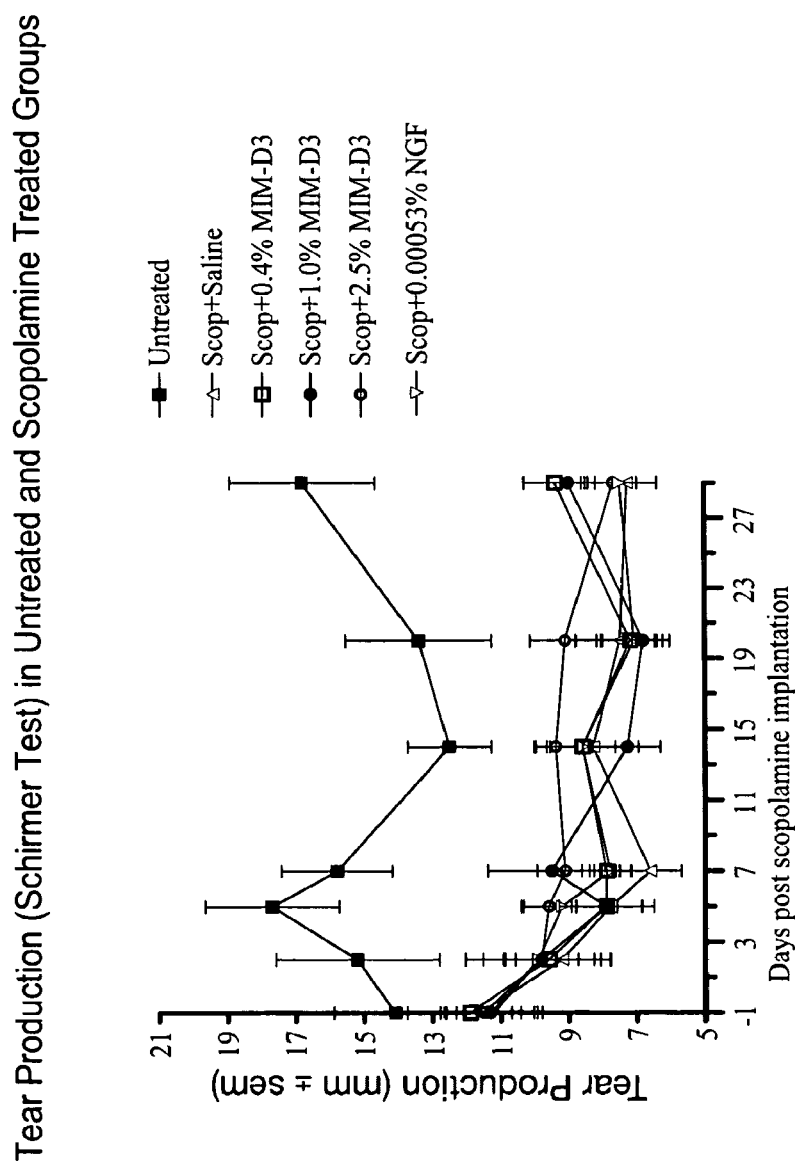
FIG. 22 is a plot of tear production (mm±sem) (Y axis) in naïve and scopolamine implanted rats treated with saline, compound D3 at 0.4%, 1.0%, 2.5%, and 0.00053% NGF in days post scopolamine implantation (X axis).

The mean presurgical Schirmer tear test for 30 rats (60 eyes) was 11.9±3.8 mm (p=0.7228). After 2 days, scopolamine treated animals had lower Schirmer scores (i.e. less tears) than untreated controls (9.6±3.2 mm compared to 15.2±5.4 mm, p=0.1671), and animals were allocated into groups (Table 7). At Day 5, treated animals had an average Schirmer score of 8.5±2.2 mm compared to untreated controls (17.7±4.4 mm) and this difference was statistically significant (p<0.0001), corresponding to dry eye induction. At subsequent examinations, the groups receiving scopolamine had statistically significant lower Schirmer scores than untreated control (G1) (p<0.0001 to 0.0541-borderline at day 14), with no statistically significant difference among the groups that received scopolamine (Table 8 and FIG. 22).

TABLE 7

Group Allocation

| Group [2][a] | Schirmer's Test (mm ± SD) | |
|---|---|---|
| | Day −1 | Day 2 |
| 1 | 14.1 ± 4.3 | 15.2 ± 5.2 |
| 2 | 11.6 ± 3.6 | 9.2 ± 3.6 |
| 3 | 11.9 ± 4.4 | 9.6 ± 3.0 |
| 4 | 11.3 ± 4.5 | 9.8 ± 4.0 |
| 5 | 11.5 ± 2.2 | 9.8 ± 2.4 |
| 6 | 11.2 ± 3.7 | 9.9 ± 4.9 |

[a] n = 5 at every observation
[2] Group Code:
1) Naive;
2) Scopolamine + Saline;
3) Scopolamine + 0.4% Compound D3;
4) Scopolamine + 1.0% Compound D3;
5) Scopolamine + 2.5% Compound D3;
6) Scopolamine + 0.00053% NGF

TABLE 8

Schirmer Test Data

| | Schirmer's Test (mm ± SD) | | | | | | |
|---|---|---|---|---|---|---|---|
| | Groups[3][a] | | | | | | |
| Day | 1 | 2 | 3 | 4 | 5 | 6 | P value |
| −1 | 14.1 ± 4.0 | 11.6 ± 2.6 | 11.9 ± 4.2 | 11.3 ± 3.0 | 11.5 ± 1.8 | 11.2 ± 3.2 | 0.7228 |
| 2 | 15.2 ± 5.4 | 9.2 ± 3.1 | 9.6 ± 3.0 | 9.8 ± 3.8 | 9.8 ± 2.4 | 9.9 ± 4.8 | 0.1671 |
| 5 | 17.7 ± 4.4 | 7.8 ± 0.4 | 7.9 ± 3.2 | 7.9 ± 2.3 | 9.6 ± 1.8 | 9.2 ± 2.5 | <0.0001 |
| 7 | 15.8 ± 3.6 | 6.6 ± 2.1 | 7.9 ± 1.6 | 9.5 ± 4.2 | 9.1 ± 1.9 | 7.8 ± 1.4 | 0.0002 |
| 14 | 12.5 ± 2.7 | 8.3 ± 3.0 | 8.6 ± 3.0 | 7.3 ± 2.3 | 9.4 ± 1.4 | 8.6 ± 2.1 | 0.0541 |
| 20 | 13.4 ± 4.8 | 7.5 ± 2.9 | 7.2 ± 1.8 | 6.8 ± 0.8 | 9.1 ± 2.3 | 7.1 ± 2.4 | 0.0075 |
| 29 | 16.8 ± 4.8 | 7.3 ± 2.0 | 9.4 ± 2.0 | 9.0 ± 2.9 | 7.7 ± 1.6 | 7.5 ± 2.5 | 0.0001 |

[a] n = 5 at every observation
[3] Group Code:
1) Naive;
2) Scopolamine + Saline;
3) Scopolamine + 0.4% Compound D3;
4) Scopolamine + 1.0% Compound D3;
5) Scopolamine + 2.5% Compound D3;
6) Scopolamine + 0.00053% NGF Tear Fluorescein Clearance:

Tear fluid turnover was measured using the fluorescein clearance test on days 5, 7, 14 and 20 post induction of dry eye. Tear fluorescein clearance was evaluated as described for humans (Alfonso, A. A., et al., "Correlation of Tear Fluorescein Clearance and Schirmer Test Scores with Ocular Irritation Symptoms," *Ophthalmology* 106:803-810 (1999), which is incorporated herein by reference in its entirety) and modified for rats (Chen, W., et al., "Keratoconjunctivitis Sicca Modifies Epithelial Stem Cell Proliferation Kinetics in Conjunctiva," *Cornea* 26:1101-1106 (2007), which is incorporated herein by reference in its entirety). Animals were lightly sedated with Isoflurane and two microliters of 1% sodium fluorescein (Sigma-Aldrich, St. Louis, Mo.) solution (in sterile saline) was applied to the lower conjunctival sac. The animals awoke within two minutes. After fifteen minutes, the animals were re-sedated and the fluorescein-stained tear fluid was collected with a phenol-red cotton thread (as described for Schirmer testing). The threads were immediately sealed in 1.5 mL polypropylene Eppendorf tubes shielded from light until fluorophotometric analysis. The volume of the collected tear fluid was determined by the length of cotton wetting in mm. After, 100 µl of phosphate-buffered saline (PBS) was added, the tubes were spun at 12,000 rpm for five minutes and the fluid transferred to a 96-well polystyrene microtiter plate (Corning Life Sciences #2592, Fisher Scientific, Nepean, Ontario). A standard well was prepared on each plate, which consisted of a phenol-red thread placed in 100 µl PBS containing 2 µl of 1% sodium fluorescein solution. Fluorescence was measured immediately using a fluorescence microplate reader (FLUOstar OPTIMA, BMG Labtech, Germany) after setting the gain to the standard well. The concentration of fluorescein in tears was calculated from the fluorescence units divided by the mm of cotton wetting (Fu/mm).

Figure 23:
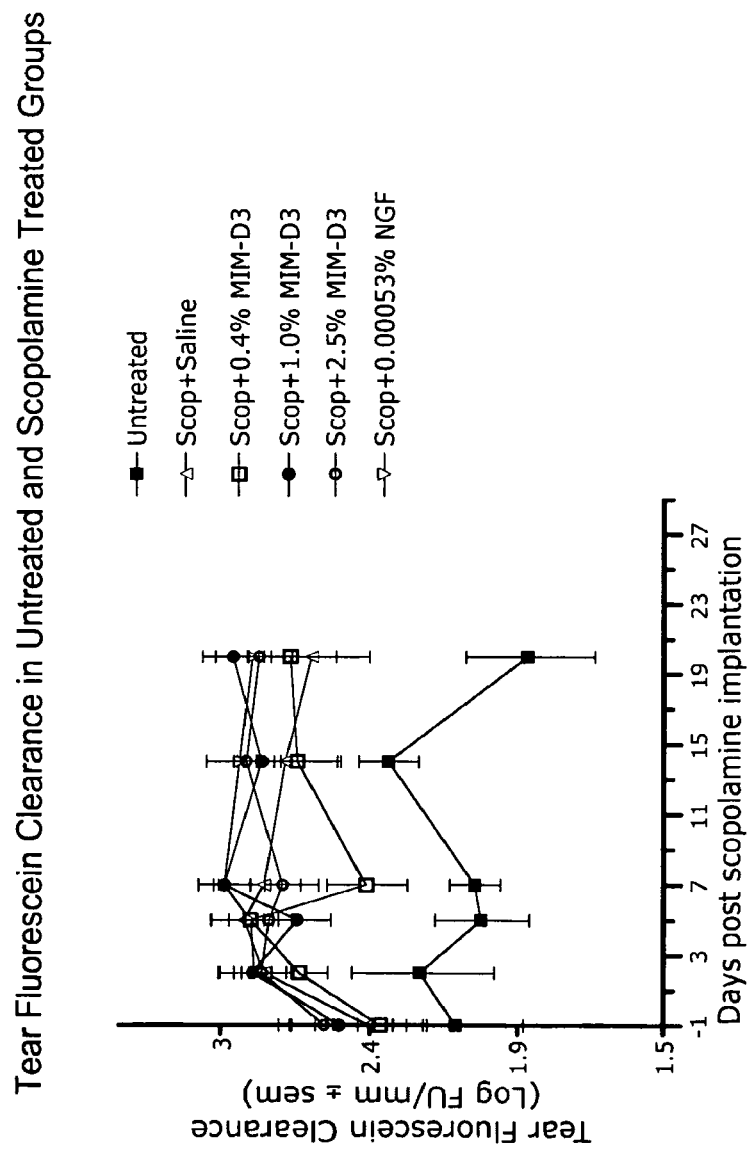
FIG. 23 is a plot of tear fluorescein clearance (Log FU/mm±sem) in naïve and scopolamine implanted rats treated with saline, compound D3 at 0.4%, 1.0%, 2.5%, and 0.00053% NGF in days post scopolamine implantation (X axis).

At baseline, the mean fluorescein clearance value was 387±427 FU/mm (p=0.7506). At subsequent examinations, numerically, the groups receiving scopolamine had higher values (i.e., less tear turnover) than the Group 1 (untreated control). This difference was statistically significant at day 7 (0.0378), but not other days (p=0.1242 to 0.4472). There was no statistically significant difference among the groups that received scopolamine (Table 9 and FIG. 23).

TABLE 9

Tear Fluorescein Clearance Data

| | Tear Fluorescein Clearance (FU/mm ± SD) | | | | | | |
|---|---|---|---|---|---|---|---|
| | Groups[4][a] | | | | | | |
| Day | 1 | 2 | 3 | 4 | 5 | 6 | P value |
| −1 | 178 ± 151 | 372 ± 409 | 288 ± 247 | 575 ± 682 | 428 ± 312 | 483 ± 562 | 0.7506 |
| 2 | 282 ± 308 | 699 ± 389 | 516 ± 305 | 880 ± 673 | 777 ± 592 | 933 ± 824 | 0.4472 |

TABLE 9-continued

Tear Fluorescein Clearance Data

Tear Fluorescein Clearance (FU/mm ± SD)

| | Groups[4a] | | | | | | |
|---|---|---|---|---|---|---|---|
| Day | 1 | 2 | 3 | 4 | 5 | 6 | P value |
| 5 | 120 ± 69 | 1018 ± 874 | 969 ± 732 | 550 ± 369 | 671 ± 344 | 804 ± 432 | 0.1377 |
| 7 | 113 ± 49 | 1058 ± 1101 | 296 ± 156 | 1098 ± 639 | 561 ± 231 | 1080 ± 572 | 0.0378 |
| 14 | 228 ± 119 | 779 ± 759 | 635 ± 599 | 686 ± 306 | 791 ± 235 | 1097 ± 1112 | 0.4245 |
| 20 | 96 ± 66 | 659 ± 746 | 667 ± 508 | 1067 ± 773 | 673 ± 170 | 861 ± 414 | 0.1242 |

[a]n = 5 at every observation
[4]Group Code:
1) Naive;
2) Scopolamine + Saline;
3) Scopolamine + 0.4% Compound D3;
4) Scopolamine + 1.0% Compound D3;
5) Scopolamine + 2.5% Compound D3;
6) Scopolamine + 0.00053% NGF A significant inverse correlation was noted between tear fluorescein clearance values and Schirmer test values between groups at all examinations. Tear fluorescein concentration increased as aqueous tear production decreased (Spearman r=−0.3306, p<0.0001, n=180 XY pairs).

Figure 24:
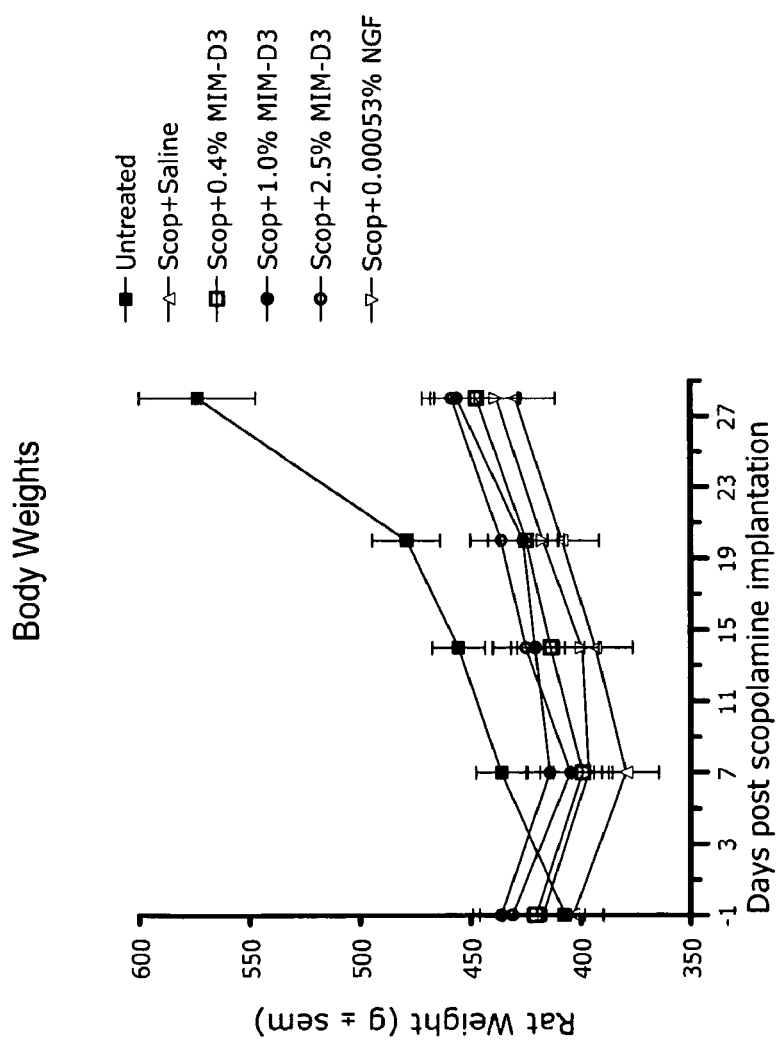
FIG. 24 is a graph of body weight (g±sem) (Y axis) for naïve untreated control rats, scopolamine implanted rats treated with saline, compound D3 at 0.4%, 1.0%, 2.5%, and 0.00053% NGF in days post scopolamine implantation (X axis).

Effect of Scopolamine in Rats:

There were no mortalities. Mild to severe ocular irritation was observed in all scopolamine treated animals (G2-6) from Day 2 onward. Most scopolamine treated animals eyes showed conjunctival congestion, swelling and conjunctival bloody discharge. Conjunctival congestion and conjunctival bloody discharge usually resolved the next day, but conjunctival swelling continued throughout the study. Pre-treatment, mean body weight was approximately 400 g, and was not statistically different among groups (p=0.3927) (Table 10). Mean body weight in the untreated control groups (G1) increased to approximately 575 g throughout the study. In the five groups receiving scopolamine (G2-G6), mean body weight increased to approximately 425 to 450 g. There was a statistically significant effect of treatment to decrease body weight starting on Day 14, continuing through Day 28 (p<0.0001 to 0.0426) (FIG. 24).

characterize the data for each study group. A two-way analysis of variance was performed for body weight and the ophthalmic signs with factors of treatment group, examination day, and treatment group examination day (PROC GLM) (PC-SAS, version 9.1, SAS Institute, Cary N.C.). When stratified by examination day, when the treatment group was statistically significant (p<0.05, two-tail), pair wise comparisons were performed. For comparison to the untreated control (Group 1), LSMEANS with Dunnett's adjustment was used. For comparison between other groups, LSMEANS was used. The among group p values are indicated in the data tables and the inferential p values for all pair wise comparisons were assessed (data not included). The Spearman correlation coefficient by rank was used to evaluate correlation between various endpoint measurements using GraphPad Prism 4.0c (GraphPad Software Inc., La Jolla, Calif.).

A posteriori, a power calculation was performed. Whitley, E. and Ball, J., "Statistics Review 4: Sample Size Calculations," *Critical Care*, 6:335-341 (2002), which is incorporated herein by reference in its entirety. The study had 80% power (beta) (with an alpha=0.05 two tailed) to detect a

TABLE 10

Body Weights

Body Weights (g ± SD)

| | Groups[1a] | | | | | | |
|---|---|---|---|---|---|---|---|
| Day | 1 | 2 | 3 | 4 | 5 | 6 | P value |
| −1 | 407 ± 20 | 403 ± 31 | 421 ± 34 | 436 ± 29 | 431 ± 33 | 417 ± 16 | 0.3927 |
| 7 | 436 ± 25 | 379 ± 33 | 399 ± 30 | 414 ± 23 | 405 ± 32 | 396 ± 20 | 0.0648 |
| 14 | 456 ± 27 | 393 ± 38 | 407 ± 35 | 424 ± 27 | 425 ± 33 | 399 ± 18 | 0.0426 |
| 20 | 479 ± 34 | 409 ± 39 | 416 ± 38 | 430 ± 27 | 436 ± 30 | 417 ± 16 | 0.0261 |
| 29 | 574 ± 59 | 430 ± 41 | 440 ± 36 | 460 ± 30 | 459 ± 29 | 438 ± 22 | <0.0001 |

[a]n = 5 rats at every observation
[1]Group Code:
1) Naive;
2) Scopolamine + Saline;
3) Scopolamine + 0.4% Compound D3;
4) Scopolamine + 1.0% Compound D3;
5) Scopolamine + 2.5% Compound D3;
6) Scopolamine + 0.00053% NGF Statistical Analysis When applicable, eye data were averaged for each rat, and therefore the experimental animal became the unit analyzed (n=5). The mean and standard deviation (SD) were used to difference as small as 54 g in body weight, 4.9 mm in Schirmer score, 830 FU/mm in fluorescein clearance, 2.8 seconds in tBUT, 0.9 score in corneal staining, and 4.5 ng/μL mucin.

What is claimed is:

1. A viscous ophthalmic composition formulated as a solution, ointment, cream, lotion, eye drop or eye gel, comprising a thickener and a β-turn peptidomimetic cyclic compound represented by Formula D3:

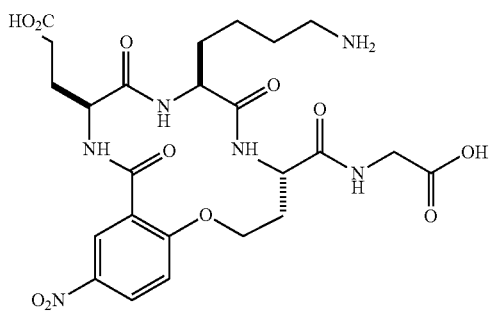 [SMILES: NCCCC[C@@H]1NC(=O)[C@H](CCC(=O)O)NC(=O)c2cc([N+](=O)[O-])ccc2OCC[C@@H](C(=O)NCC(=O)O)NC1=O]

or a pharmaceutically acceptable salt thereof, wherein the compound represented by Formula D3 or salt thereof is in an amount of 0.001 to 2.5 (w/v) %.

2. The viscous ophthalmic composition of claim 1, wherein the composition comprises a phosphate buffer.

3. The viscous ophthalmic composition of claim 1, wherein the composition comprises sodium chloride.

4. The viscous ophthalmic composition of claim 1, wherein the composition comprises phosphate buffered saline.

5. The viscous ophthalmic composition of claim 1, wherein the thickener comprises hydroxethylcellulose, hydroxypropylcellulose, methylcellulose, hydroxypropylmethylcellulose, carboxymethylcellulose, or a salt thereof.

6. The viscous ophthalmic composition of claim 1, further comprising an isotonizing agent.

7. The viscous ophthalmic composition of claim 6, wherein the isotonizing agent comprises a sugar or polyhydric alcohol.

8. The viscous ophthalmic composition of claim 1, further comprising a solubilizer.

9. The viscous ophthalmic composition of claim 8, wherein the solubilizer is selected from the group consisting of a cyclodextrin, a water soluble polymer, and a surfactant.

10. A viscous ophthalmic composition comprising an ointment base and a β-turn peptidomimetic cyclic compound represented by Formula D3:

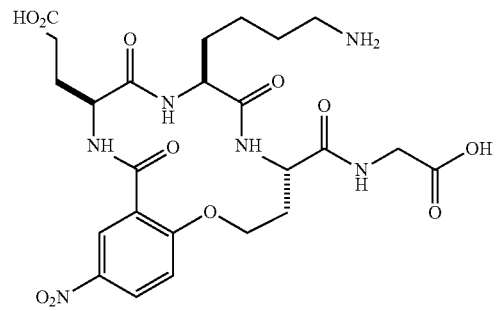 [SMILES: NCCCC[C@@H]1NC(=O)[C@H](CCC(=O)O)NC(=O)c2cc([N+](=O)[O-])ccc2OCC[C@@H](C(=O)NCC(=O)O)NC1=O]

or a pharmaceutically acceptable salt thereof, wherein the compound represented by Formula D3 or salt thereof is in an amount of 0.001 to 2.5 (w/v) %.

11. The viscous ophthalmic composition of claim 10, wherein the ointment base is selected from the group consisting of lanolin, petroleum jelly, plastibase, liquid paraffin, and polyethylene glycol.

12. The viscous ophthalmic composition of claim 1, formulated as a solution.

13. The viscous ophthalmic composition of claim 1, formulated as an eye drop.

14. The viscous ophthalmic composition of claim 1, wherein the compound represented by Formula D3 or salt thereof is in an amount of 0.02 to 2.0 (w/v) %.

15. The viscous ophthalmic composition of claim 1, wherein the compound represented by Formula D3 or salt thereof is in an amount of 0.03 to 1.5 (w/v) %.

16. The viscous ophthalmic composition of claim 1, wherein the compound represented by Formula D3 or salt thereof is in an amount of 0.05 to 1.0 (w/v) %.

17. The viscous ophthalmic composition of claim 1, wherein the compound represented by Formula D3 or salt thereof is in an amount of 1.0 (w/v) %.

18. The viscous ophthalmic composition of claim 10, wherein the compound represented by Formula D3 or salt thereof is in an amount of 0.02 to 2.0 (w/v) %.

19. The viscous ophthalmic composition of claim 10, wherein the compound represented by Formula D3 or salt thereof is in an amount of 0.03 to 1.5 (w/v) %.

20. The viscous ophthalmic composition of claim 10, wherein the compound represented by Formula D3 or salt thereof is in an amount of 0.05 to 1.0 (w/v) %.

21. The viscous ophthalmic composition of claim 10, wherein the compound represented by Formula D3 or salt thereof is in an amount of 1.0 (w/v) %.

* * * * *

UNITED STATES PATENT AND TRADEMARK OFFICE
CERTIFICATE OF CORRECTION

PATENT NO. : 8,748,391 B2  
APPLICATION NO. : 13/601258  
DATED : June 10, 2014  
INVENTOR(S) : Garth Cumberlidge et al.

Page 1 of 1

It is certified that error appears in the above-identified patent and that said Letters Patent is hereby corrected as shown below:

On Title Page, Item (75) Inventors, after "(CA)"

add Horacio Uri Saragovi, Montreal (CA).

Signed and Sealed this  
Twelfth Day of July, 2016

Michelle K. Lee  
*Director of the United States Patent and Trademark Office*